US012763204B2

(12) United States Patent
Alam

(10) Patent No.: US 12,763,204 B2
(45) Date of Patent: Oct. 13, 2026

(54) PATIENT MONITORING USING ARTIFICIAL INTELLIGENCE ASSISTANTS

(71) Applicant: MatrixCare, Inc., Bloomington, MN (US)

(72) Inventor: Samia Sadeque Alam, Houston, TX (US)

(73) Assignee: MatrixCare, Inc., Bloomington, MN (US)

( * ) Notice: Subject to any disclaimer, the term of this patent is extended or adjusted under 35 U.S.C. 154(b) by 96 days.

(21) Appl. No.: 18/172,096

(22) Filed: Feb. 21, 2023

(65) Prior Publication Data

US 2023/0317274 A1 Oct. 5, 2023

Related U.S. Application Data

(60) Provisional application No. 63/362,246, filed on Mar. 31, 2022.

(51) Int. Cl.

| | |
|---|---|
| ***G16H 40/67*** | (2018.01) |
| ***G06F 40/40*** | (2020.01) |
| ***G16H 10/20*** | (2018.01) |
| ***G16H 50/20*** | (2018.01) |

(52) U.S. Cl.

CPC ............. *G16H 40/67* (2018.01); *G06F 40/40* (2020.01); *G16H 10/20* (2018.01); *G16H 50/20* (2018.01)

(58) Field of Classification Search

CPC ........ G16H 40/67; G16H 50/20; G16H 10/20; G06F 40/40

See application file for complete search history.

(56) References Cited

U.S. PATENT DOCUMENTS

| | | | | |
|---|---|---|---|---|
| 11,599,830 | B1 * | 3/2023 | Nudd | G06N 20/00 |
| 2007/0276270 | A1 * | 11/2007 | Tran | A61B 5/0022 600/508 |
| 2019/0043619 | A1 * | 2/2019 | Vaughan | G16H 20/70 |
| 2019/0385711 | A1 * | 12/2019 | Shriberg | G09B 19/00 |
| 2020/0380957 | A1 * | 12/2020 | Edwards | G16H 50/20 |
| 2021/0027759 | A1 * | 1/2021 | Ogawa | G10L 13/02 |
| 2021/0110895 | A1 * | 4/2021 | Shriberg | G06F 40/20 |
| 2021/0133509 | A1 * | 5/2021 | Wall | G06F 18/285 |
| 2021/0375278 | A1 * | 12/2021 | Hatambeiki | G16H 50/20 |

(Continued)

FOREIGN PATENT DOCUMENTS

| | | | | |
|---|---|---|---|---|
| CN | 105792752 A | * | 7/2016 | A61B 5/16 |
| CN | 108780663 A | * | 11/2018 | A61B 5/0022 |

(Continued)

OTHER PUBLICATIONS

Fraser et al., "Measuring Cognitive Status from Speech in a Smart Home Environment," Sep. 2021, IEEE Instrumentation & Measurement Magazine, pp. 13-21) (Year: 2021).*

*Primary Examiner* — Kenneth Bartley

(74) *Attorney, Agent, or Firm* — Patterson + Sheridan, LLP

(57) ABSTRACT

Embodiments herein include methods and a device to track and monitor a patient's condition over time to detect a change in a patient condition (including cognitive decline) using personal artificial intelligence (AI) assistant devices. The present embodiments use functionalities of the assistant devices by engaging with a monitored patient and tracking changes in a patient's condition overtime using various learning models to detect changes in the patient's speech, mood, and other conditions.

14 Claims, 16 Drawing Sheets

(56) References Cited

U.S. PATENT DOCUMENTS

| | | | | | |
|---|---|---|---|---|---|
| 2022/0328064 | A1* | 10/2022 | Shriberg | ................. | G10L 25/66 |
| 2022/0375467 | A1* | 11/2022 | Jin | .......................... | G10L 15/22 |
| 2023/0092866 | A1* | 3/2023 | Vaughan | .................. | G06N 5/01<br>706/12 |
| 2024/0112808 | A1* | 4/2024 | Strader | .................. | G16H 50/20 |
| 2024/0170109 | A1* | 5/2024 | Shriberg | ................ | G09B 19/00 |

FOREIGN PATENT DOCUMENTS

| | | | | | | |
|---|---|---|---|---|---|---|
| CN | 109697283 | A | * | 4/2019 | ......... | G06F 3/04817 |
| CN | 110192252 | A | * | 8/2019 | ............. | G06N 20/00 |
| CN | 111223553 | A | * | 6/2020 | ......... | G06K 9/00885 |
| EP | 4276655 | A1 | * | 11/2023 | ......... | G06F 16/2477 |
| JP | 2021529382 | A | * | 10/2021 | | |

* cited by examiner

PATIENT MONITORING USING ARTIFICIAL INTELLIGENCE ASSISTANTS

CROSS-REFERENCE TO RELATED APPLICATIONS

This application claims priority to U.S. Provisional Patent Application No. 63/362,246, filed Mar. 31, 2022, the entire content of which is incorporated herein by reference in its entirety.

INTRODUCTION

Embodiments of the present disclosure relate to audio recognition including natural language processing. More particularly, a personal artificial intelligence assistant is used to build a model for learning and tracking a patient's speech and language patterns to detect changes in speech patterns and other indicative language information to determine changes in the patient's overall cognitive health and health condition.

Various technologies exist that allow for a person to call for assistance when in distress, but require the person to activate a call response (e.g., press one or more buttons) or rely on vital sign monitoring (e.g., an electrocardiogram) to trigger a call-worthy condition before assistance is requested. However, some conditions, such as gradual cognitive decline, occur over long periods of time and may not present as recognized emergency situations. Accordingly, various vulnerable persons need non-intrusive technologies that allow for passive monitoring and assistance.

SUMMARY

Certain embodiments provide a method that includes at a first time, capturing, via an artificial intelligence (AI) assistant device, first audio from an environment, detecting first utterances from the first audio for a patient, and adding the first utterances to a language tracking model. The method also includes at a second time, capturing, via the AI assistant device, second audio from the environment, detecting second utterances from the second audio for the patient, detecting via a language tracking engine provided by the AI assistant device, the language tracking model, and the second utterances, a condition change indicating a condition of the patient has changed from the first time to the second time, and generating a condition notification may include the condition change. Other embodiments of this aspect include corresponding computer systems, apparatus, and computer programs recorded on one or more computer storage devices, each configured to perform the actions of the methods.

Other embodiments provide a non-transitory computer-readable storage medium including computer-readable program code that when executed using one or more computer processors, performs an operation. The operation includes at a first time, capturing, via an artificial intelligence (AI) assistant device, first audio from an environment, detecting first utterances from the first audio for a patient, and adding the first utterances to a language tracking model. The operation also includes at a second time, capturing, via the AI assistant device, second audio from the environment, detecting second utterances from the second audio for the patient, detecting via a language tracking engine provided by the AI assistant device, the language tracking model, and the second utterances, a condition change indicating a condition of the patient has changed from the first time to the second time, and generating a condition notification may include the condition change.

Other embodiments provide an artificial assistant device. The artificial assistant device includes one or more computer processors and a memory containing a program which when executed by the processors performs an operation. The operation includes at a first time, capturing, via the artificial intelligence (AI) assistant device, first audio from an environment, detecting first utterances from the first audio for a patient, and adding the first utterances to a language tracking model. The operation also includes at a second time, capturing, via the AI assistant device, second audio from the environment, detecting second utterances from the second audio for the patient, detecting via a language tracking engine provided by the AI assistant device, the language tracking model, and the second utterances, a condition change indicating a condition of the patient has changed from the first time to the second time, and generating a condition notification may include the condition change.

DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Embodiments herein determine when to place, and then placing, a passive assistive call using personal artificial intelligence (AI) assistants. Assistant devices, by which various personal AI assistants are deployed, offer several benefits over previous assistive call systems, including the ability to use audio recorded in the environment to passively assess the condition of the persons in the environment over both short term and long term time frames. The assistant device may be in communication with various other sensors to enhance or supplement the audio assessment of the persons in the environment, and may be used in a variety of scenarios where prior monitoring and call systems struggled to quickly and accurately identify immediate distress in various monitored persons (e.g., patients) or mounting distress such as gradual health condition or cognitive decline (e.g., caused by minor strokes and other cognitive decline).

AI assistants such as provide a bevy of services to their users. These services can include responding to voice-activated requests (e.g., responding via audio to a request for the day's forecast with a local weather prediction), integrating with a human user's calendar, controlling appliances or lights, placing phone calls, or the like. These AI assistants often reside partially on a local device, as a local client, and partially in a back-end service located remotely (e.g., in a cloud server) from the local device. The local client handles data collection, some preprocessing, and data output, while the back-end service may handle speech recognition, natural language processing, and data fetching (e.g., looking up the requested weather forecast).

However, assistant devices, although beneficial in the environment, are active devices that often require the users to speak an utterance with a cue phrase to activate the device, or require active input from the users to perform various tasks. Accordingly, although the assistant device can be unobtrusive, and users may seek to incorporate the assistant devices in various environments, the assistant devices often purposely exclude audio not related to human speech from collection and analysis. In contrast, the present disclosure improves upon the base functionalities of the assistant devices by routinely and actively engaging with a user to determine and set baseline health and cognitive conditions and monitor the user over time to detect any potential changes in the overall condition or health of the user.

Accordingly, the present disclosure provides for improved functionality in assistant devices and devices linked to the assistant devices, improved processing speed, improved data security, and improved outcomes in healthcare (including prophylactic care and improved accuracy in diagnoses and treatments).

Example Use Environment

Figure 1:
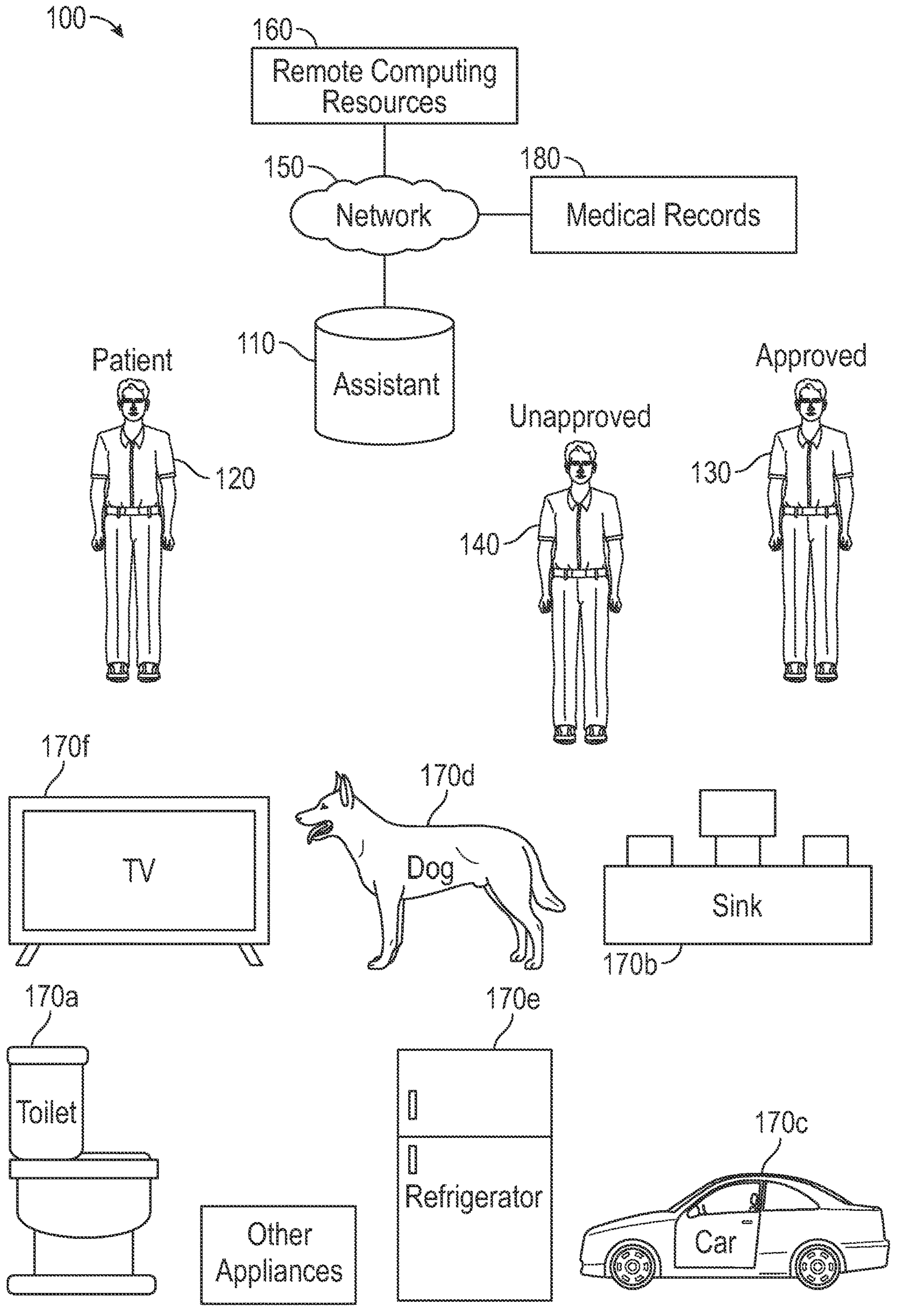
FIG. 1 illustrates an environment in which an assistant device, hosting a local client for an AI assistant, may be deployed to interact with various persons, according to embodiments of the present disclosure.

FIG. 1 illustrates an environment 100 in which the AI assistant device 110, hosting a local client for an AI assistant, may be deployed to interact with various persons, according to embodiments of the present disclosure. As discussed herein, the environment 100 is a residential environment, such as a personal home, a group home, a care facility, a community center, a car, a store, or other community area. Various persons may come and go in the environment 100 with different levels of access to health information. The environment 100 generally refers to the surrounding areas in which audio outputs of the AI assistant device 110 are comprehensible to a person of average hearing (unaided by listening devices), and the boundary of the environment 100 may be defined by a Signal to Noise Ratio (SNR) in decibels (dB) for output audio that may change as the volume of the AI assistant device 110 changes or as background noise changes.

In a healthcare context, the persons that the AI assistant device 110 may interact with include patients 120 whose health and well-being are monitored, authorized persons, including authorized person 130, who are currently authorized by the patients 120 to receive health information related to the patient 120 via the AI assistant device 110, and unauthorized persons 140 who are not currently authorized by the patients 120 receive health information related to the patient 120. In various embodiments, the authorized person 130 and the unauthorized persons 140 may be permitted to interact with the AI assistant device 110 (or denied access to the AI assistant device 110) for non-healthcare related information independently of the permissions granted/denied for receiving health information related to the patient 120. Various other objects 170*a-f* (generally or collectively, objects 170) may also be present in the environment 100 or otherwise be observable by the AI assistant device 110 including, but not limited to: toilets 170*a*, sinks 170*b*, cars 170*c*, pets 170*d*, appliances 170*e*, audio sources 170*f* (e.g., televisions or radios), etc.

As used herein, a patient 120 may be one of several persons in the environment 100 to whom medical data and personally identifiable information (PII) pertain. Generally, a patient 120 is an authorized user for accessing their own data, and may grant rights for others to also access those data or to grant additional persons the ability to access these data on behalf of the patient 120 (e.g., via medial power of attorney). For example, a patient 120 may grant a personal health assistant, a nurse, a doctor, a trusted relative, or other person (herein provider) the ability to access medical data and PII. A patient 120 may also revoke access to the medical data and PII, and may grant or revoke access to some or all of the data. Accordingly, a patient 120 is a person that the medical data and PII relate to, authorized person 130 are those with currently held rights to access some or all of the medical data and PII, and unauthorized persons 140 include those who have not yet been identified as well as those currently lacking rights to access the medical data and PII. The identification and classification of the various persons is discussed in greater detail in relation to FIG. 2.

The AI assistant device 110 offers a user interface for requesting and receiving controlled access to health information. In some embodiments, the AI assistant device 110 is an audio-controlled computing device with which the users may interact with verbally, but various other devices may also be used as a user interface to request or provide health information to authorized parties in the environment. For example, a television may be used to output health information via a video overlay, a mobile telephone may be used to receive requests via touch-input and output health information via video or audio, etc. Generally, the AI assistant device 110 can be any device capable of hosting a local instance of an AI assistant and that remains in an "on" or "standby" mode to receive requests and provide outputs related to health information while remaining available for other tasks. For example, the AI assistant device 110 may also handle home automation tasks (e.g., controlling a thermostat, lights, appliances) on behalf of a user or interface with the television to provide health information while the patient 120 is watching a program. Example hardware for the AI assistant device 110 is discussed in greater detail in regard to FIG. 9.

In various embodiments, the AI assistant device 110 captures audio in the environment 100 and, to determine how to respond to the captured audio, may locally process the audio, may be in communication with remote computing resources 160 via a network 150 to process the audio remotely, or may perform some audio processing locally and some audio processing remotely. The AI assistant device 110 may connect to the network 150 via wired technologies (e.g., wires, fiber optic cable, etc.), wireless technologies (e.g., WIFI, cellular, satellite, Bluetooth, etc.), or combinations thereof. The network 150 may be any type of communication network, including data and/or voice networks, local area networks, and the Internet.

To determine how or whether to respond to audio captured in the environment, the AI assistant device 110 may need to filter out unwanted noises from desired audio, identify the source of the audio, and determine the content of the audio. For example, if the AI assistant device 110 detects audio of a request for the next scheduled doctor's appointment for the patient 120, the AI assistant device 110 may need to determine whether the request was received from an audio source 170*f* as unwanted noise (e.g., a character speaking in a movie or television program), the patient 120, an authorized person 130 (e.g., an in-home care assistant looking up care details for the patient 120), or an unauthorized person 140 (e.g., a curious visitor without authorization to receive that information from the AI assistant device 110). Other filters may be used to identify and discard sounds made by other objects 170 in the environment 100.

In order to identify the content of the desired audio (e.g., a command to the AI assistant device 110), an audio recognition (AR) engine performs audio analysis/filtering and speech recognition on the captured audio signals and calculates a similarity between any audio identified therein and known audio samples (e.g., utterances for certain desired interactions). The AR engine then compares this similarity to a threshold and, if the similarity is greater than the threshold, the AR engine determines that a known audio cue has been received from the environment. The AR engine may use various types of speech and audio recognition techniques, such as, large-vocabulary speech recognition techniques, keyword spotting techniques, machine-learning techniques (e.g., support vector machines (SVMs)), neural network techniques, or the like. In response to identifying an audio cue, the AI assistant device 110 may then use the audio cue to determine how to next respond. Some or all of the audio processing may be done locally on the AI assistant device 110, but the AI assistant device 110 may also offload more computationally difficult tasks to the remote computing resources 160 for additional processing.

In various embodiments, the AI assistant device 110 may also access the electronic health records 180 via the network 150 or may store some of the electronic health records 180 locally for later access. The electronic health records 180 may include one or more of: medical histories for patients, upcoming or previous appointments, medications, personal identification information (PII), demographic data, emergency contacts, treating professionals (e.g., physicians, nurses, dentists, etc.), medical powers of attorney, and the like. The electronic health records 180 may be held by one or more different facilities (e.g., a first doctor's office, a second doctor's office, a hospital, a pharmacy) that the AI assistant device 110 authenticates with to receive the data. In some embodiments, the AI assistant device 110 may locally cache some of these electronic health records 180 for offline access or faster future retrieval. Additionally or alternatively, a patient 120 or authorized person 130 can locally supply the medical data, such as by requesting the AI assistant device 110 to "remind me to take my medicine every morning", importing a calendar entry for a doctor's appointment from a linked account or computer, or the like.

Additionally, the AI assistant device 110 may store identifying information to distinguish the patient 120, authorized person 130, and unauthorized persons 140 when deciding whether to share the electronic health records 180 or data based on the electronic health records 180.

Figure 2:
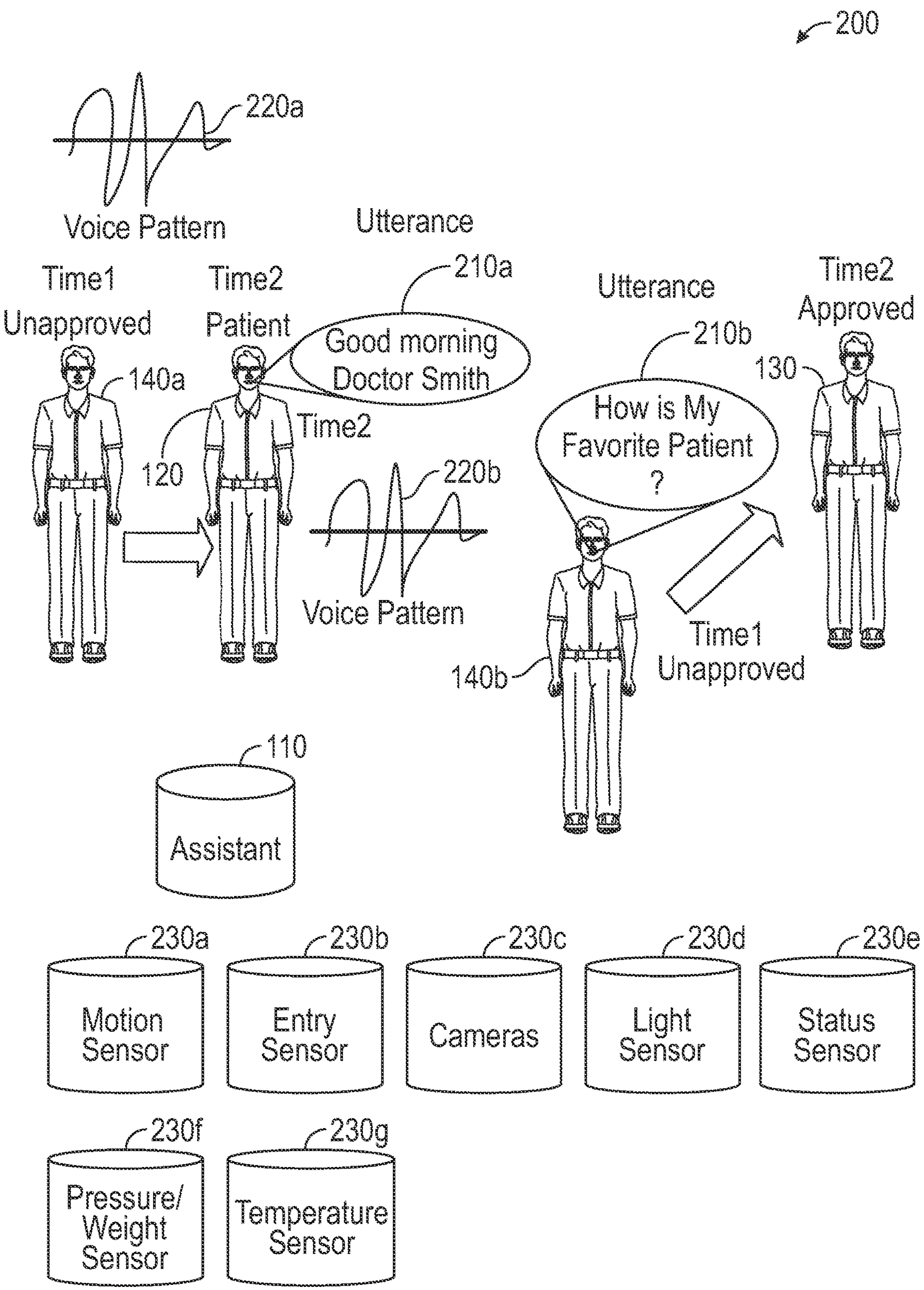
FIG. 2 illustrates an environment in which an assistant device may be deployed when identifying various parties and determining how to respond, according to embodiments of the present disclosure.

FIG. 2 illustrates an environment 200 in which the AI assistant device 110 may be deployed when identifying various parties and determining how to respond, according to embodiments of the present disclosure. The AI assistant device 110 can identify or infer the presence of a person in the environment 200 based on received audio containing speech, the sound of a door into the environment opening, or additional presence data received from sensors 230*a-g* (generally or collectively, sensors 230) in the environment, such as a motion sensor 230*a*, an entry sensor 230*b* at a doorway, cameras 230*c*, light sensors 230*d*, or the like. Other sensors 230 that may provide additional input to the AI assistant device 110 can include on/off status sensors 230*e* (e.g., for specific appliances or electrical circuits), pressure or weight sensors 230*f*, temperature sensors 230*g*, etc. The various sensors, sensors 230, may include or be part of a computing system 900 as described in greater detail in regards to FIG. 9.

Generally, until a person has been identified, the AI assistant device 110 classifies that person as an unauthorized person 140, and may ignore commands or audio from that person. For example, at Time1, the AI assistant device 110 may know that two persons are present in the environment 200, but may not know the identities of those persons, and therefore treats the first person as a first unauthorized person 140*a* and the second person as a second unauthorized person 140*b*.

In various embodiments, persons can identify themselves directly to the AI assistant device 110 or may identify other parties to the AI assistant device 110. For example, when a first utterance 210*a* (generally or collectively, utterance 210) is received from the first unauthorized person 140*a*, the AI assistant device 110 may extract a first voice pattern 220*a* (generally or collectively, voice pattern 220) from the words (including pitch, cadence, tone, and the like) to compare against other known voice patterns, such as the voice pattern 220 to identify an associated known person. In the illustrated example, the first voice pattern 220*a* matches that of a patient 120, and the AI assistant device 110 therefore reclassifies the first unauthorized person 140*a* to be the patient 120.

The AI assistant device 110 may store various identity profiles for persons to identify those persons as a patient 120, authorized person 130 for that patient, or as unauthorized persons 140 for that patient, with various levels of rights to access or provide health information for the patient 120 and various interests in collecting or maintaining data related to that person.

Once a person has been identified as a patient 120 (or other authorized party trusted to identify other persons with whom access should be granted), the AI assistant device 110 may rely on utterances 210 from that trusted person to identify other persons. For example, the first utterance 210*a* can be used to identify the first unauthorized person 140*a* as the patient 120 based on the associated first voice pattern 220*a*, and the contents of the first utterance 210*a* can be examined for information identifying the other party. In the illustrated example, the AI assistant device 110 (either locally or via remote computing resources 160) may extract the identity "Dr. Smith" from the first utterance 210*a* to identify that the second unauthorized person 140*b* is Dr. Smith, who is an authorized person 130 for the patient 120, and the AI assistant device 110 therefore reclassifies the second unauthorized person 140*b* to be an authorized person 130 for the patient 120.

Additionally or alternatively, the AI assistant device 110 may identify Dr. Smith as an authorized person 130 based on a second voice pattern 220*b* extracted from the second utterance 210*b* spoken by Dr. Smith. The voice patterns 220 may be continuously used by the AI assistance device 110 to re-identify Dr. Smith or the patient 120 (e.g., at a later time) within the environment 200 or to distinguish utterances 210 as coming from a specific person within the environment 200.

When multiple persons are present in the environment 200, and potentially moving about the environment, the AI assistant device 110 may continually reassess which person is which. If a confidence score for a given person falls below a threshold, the AI assistant device 110 may reclassify one or more persons as unauthorized persons 140 until identities can be reestablished. In various embodiments, the AI assistant device 110 may use directional microphones to establish where a given person is located in the environment 200, and may rely on the sensors 230 to identify how many persons are located in the environment 200 and where those persons are located.

Example Language Tracking Model Scenarios

Figure 3:
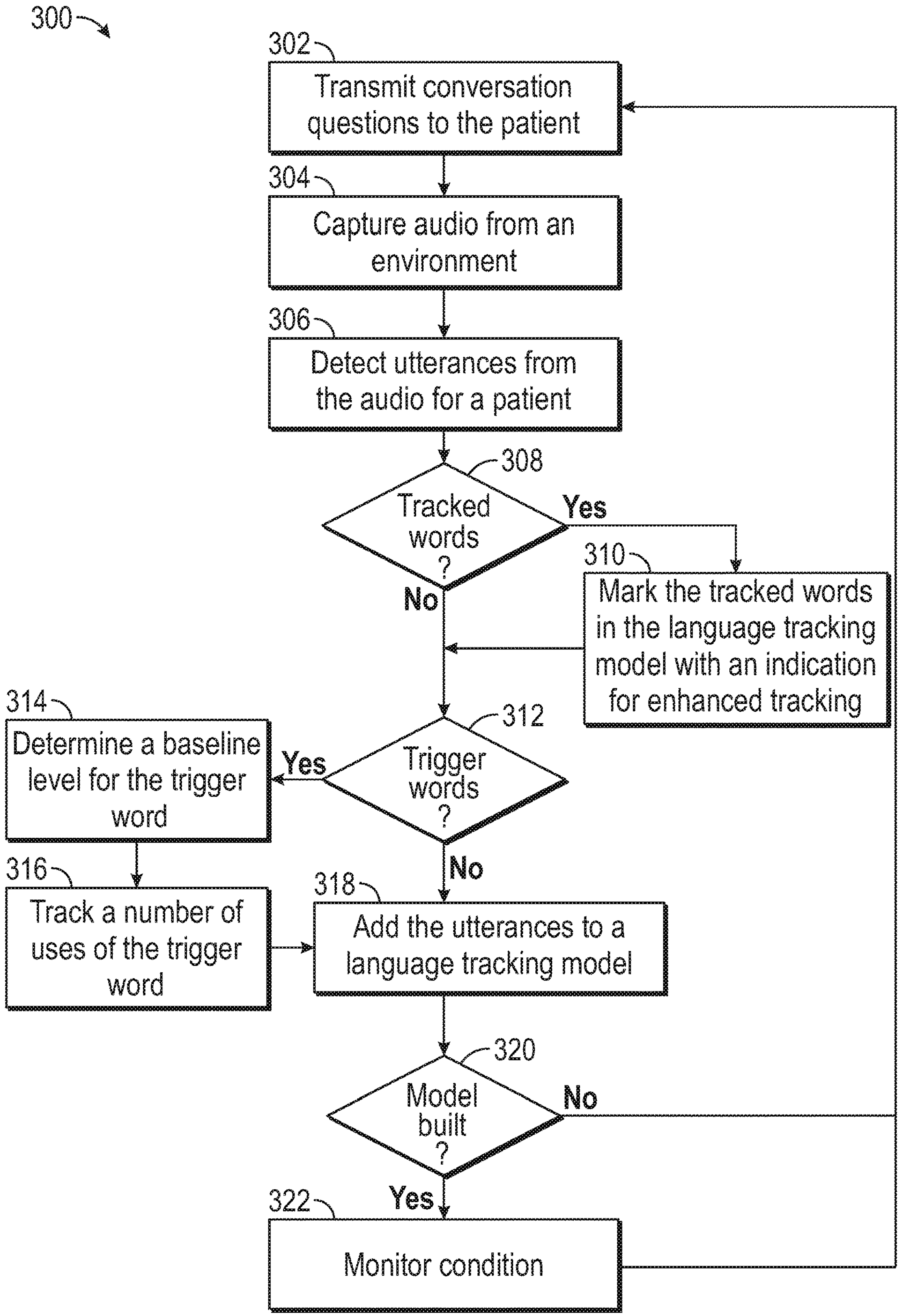
FIG. 3 is a flowchart of a method for building a language tracking model, according to embodiments of the present disclosure.

FIG. 3 is a flowchart of a method 300 for building a language tracking model, according to embodiments of the present disclosure. FIGS. 4A-4D illustrate example scenarios for how an AI assistant device may be used to build a language tracking model for a patient, according to embodiments of the present disclosure. As discussed above, the AI assistant device 110 may be utilized to monitor the health and wellbeing of the patient 120 over a long period of time. The methods and language tracking models described herein allow for granular and ongoing tracking of the speech and vocal patterns of the patient 120 to identify both long term changes and short term changes in the way the patient 120 speaks.

In some examples herein, immediate and dramatic changes to the speech and vocal patterns of the patient 120 are detected by the device 110 and indicate the patient is experiencing a medical emergency. In other examples, subtle changes occur in the patient's speech and vocal patterns over long periods of time (e.g., days, weeks, years), where the change in the condition of the patient is harder to identify based on presenting symptoms. In order to track and detect the subtle changes (as well as to enhance detection of more immediate changes) the device 110 builds/trains a language learning model discussed herein.

For ease of discussion, the steps of the method 300 are discussed with reference to FIGS. 4A-4D. As will be appreciated, the AI assistant device 110 in environment 400 of FIGS. 4A-4D may actively be used to perform specific functions requested by the patient (e.g., "tell me the weather") and call for assistance in response to receiving a command from a person in the environment 400 (e.g., "call an ambulance for me!"), and the commands issued to the AI assistant device 110 may be received from the patient 120 for themselves or from authorized persons, including authorized person 130, on behalf of the patients 120.

In each of FIGS. 4A-4D, the AI assistant device 110 is present in the environment 400 and captures audio. A machine learning model provided by the AI assistant device 110 can filter or divide the captured audio into two classes: speech sounds or utterances from the patient 120, such as utterances 420*a-n* and 440*a-n* in FIGS. 4A-4B and environmental sounds 408 (shown in FIG. 4A). The machine learning model may focus on certain frequency ranges based on demographic characteristics of the patient 120 that affect voice frequency (e.g., age, gender, smoking habits, pulmonary or vocal medical conditions) to identify a fundamental frequency (e.g., between 85 and 255 Hertz (Hz) for adults) and harmonics (e.g., between 30 and 3500 Hz for adults) therein to identify speech sounds. Frequency filtering is given as a non-limiting example for dividing captured audio into speech sounds and environmental sounds 408, but additional filtering is contemplated to identify environmental sounds 408 within the frequency range of human speech and elements of human speech outside of the main ranges used for speech.

The AI assistant device 110 provides an audio recognition (AR) engine, which may be another machine learning model or an additional layer of the filtering machine learning model. The device 110 also provide a language recognition (LR) engine 406 that builds or otherwise trains a language learning model, such as model 405. The model 405 may be any type of machine learning model, such as a neural network or other type of network. In some examples, where the patient 120 actively and frequently engages with the device 110, the device 110 trains the model 405 without needing to prompt the patient 120 for speech. In some examples, the model 405 is generated and trained using conversation questions from the AI assistant device 110, where the conversation questions are configured to generate audio responses including conversation answers, from the patient 120. In some examples, the conversation questions are generated by the device 110 in order to entice the patient 120 to engage with the device 110 such that the device 110 may passively train the model 405.

For example, the conversation questions may include a greeting and service offering that generally elicit a response from the patient 120. The conversation questions can be the same during each scenario or time shown in FIGS. 4A-4D. For example, audio outputs 410*a* are a standard greeting such as "hello, how are you today?" The audio output 410*a* and other audio outputs 430*a-d* may also vary based on responses from patient 120, the time of day, season, etc., where the AI assistant device 110, using AI models, determines and generates the various audio outputs.

In addition to processing and classifying the environmental sounds 408 and listening for answers to conversation questions/output audio, in some embodiments, the audio recognition engine may include speech recognition for various key phrases. For example, various preloaded phrases may be preloaded for local identification by the AI assistant device 110, such as, a name of the AI assistant to activate the AI assistant device 110 (e.g., "Hey, ASSISTANT") or phrases to deactivate the AI assistant device 110 (e.g., "never mind", "I'm fine", "cancel request", etc.). The AI assistant device 110 may offload further processing of speech sounds to a speech recognition system offered by remote computing resources 160 to identify the contents and intents of the various utterances from the patient 120 captured in the environment 400.

Referring to back to FIG. 3, the method 300 begins at block 302 where the AI assistant device 110 begins building/training the model 405 by transmitting conversation questions to the patient. In some examples, the AI assistant device 110 transmits the conversation questions at regular time intervals in order to build a baseline or initial condition for the patient 120. For example, the device 110 transmits the conversation questions every morning, every other day, more frequently, or less frequently depending on the needs of the patient 120 and the training status of the model 405. At block 304, the AI assistant device 110 captures audio from the environment 400 and detects utterances from the first audio for the patient 120 at block 306 as shown in FIG. 4A.

Figure 4A:
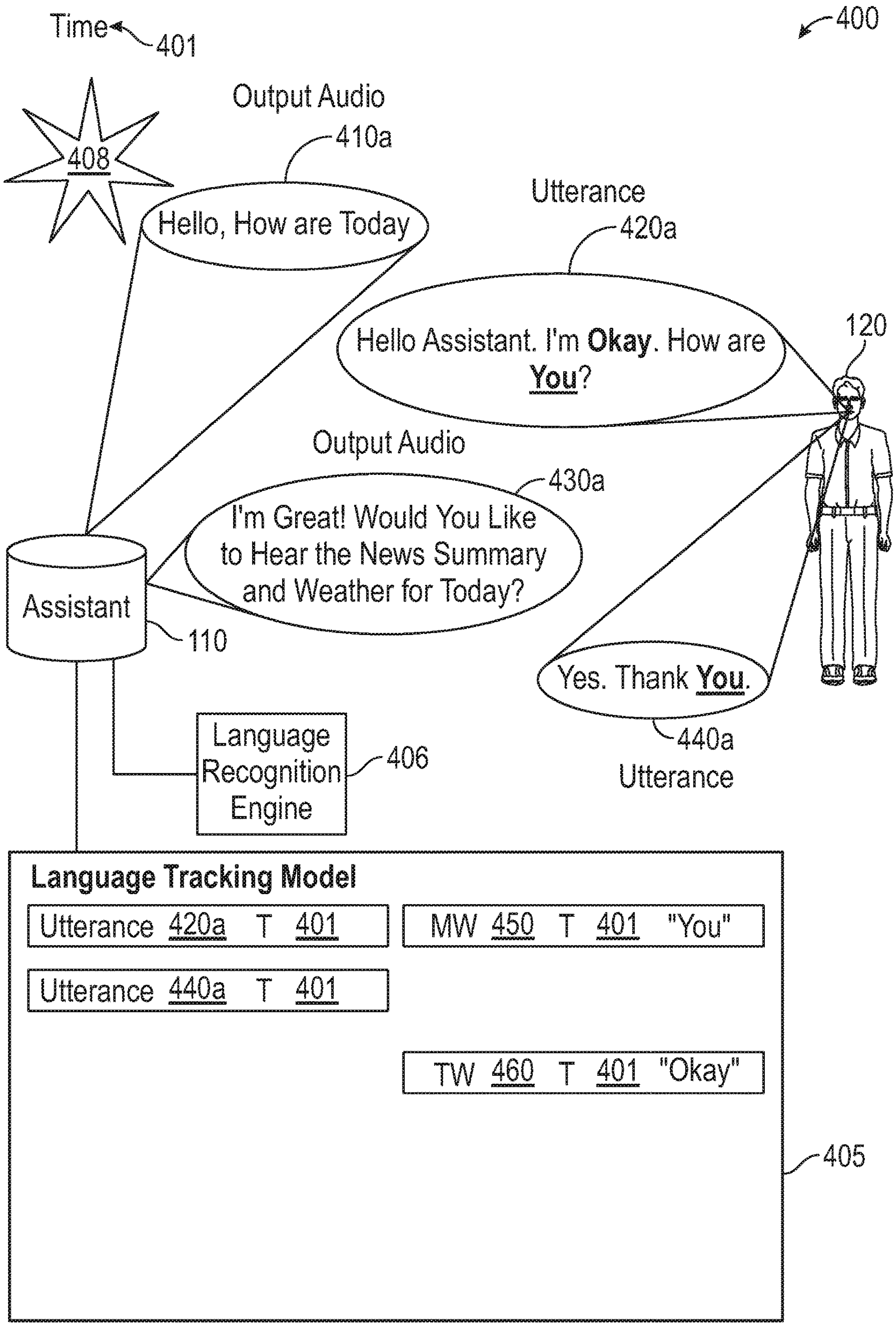
FIGS. 4A-4D illustrate example scenarios for how an AI assistant device may be used to build a language tracking model for a patient, according to embodiments of the present disclosure.

FIG. 4A illustrates a first time, time 401, where the AI assistant device 110 captures audio from the environment 400 which is used to build the model 405. As illustrated, the AI assistant device 110 outputs conversation questions including output audio 410*a*. The patient 120 responds to the AI assistant device 110 with utterance 420*a* which includes “Hello Assistant. I’m okay. How are you?” and utterance 440*a* which includes “Yes. Thank you.” As described above, the AI assistant device 110 determines that the utterances 420*a* and 440*a* are spoken by the patient 120 and not background or environment noise such as environmental sounds 408.

At block 308, the AI assistant device 110 detects, via natural language processing, tracked words in the first utterances at the time 401, including the utterances 420*a* and 440*a*. In some examples, tracked words are words that are expected to be spoken by the patient 120 frequently. For example, the patient 120 is expected to respond to or refer to the AI assistant device 110 using “you,” among other uses of the word “you” in utterances from the patient 120. In some examples, the tracked words may be preconfigured/preset by the AI assistant device 110. The tracked words may also be determined based on the patient 120. For example, if the patient 120 frequently uses a word when communicating with the device 110, that word may be added to the tracked words list. When the AI assistant device 110 detects the tracked words, method 300 proceeds to block 310 where the AI assistant device 110 marks the tracked words for tracking in the model 405 with an indication for enhanced tracking.

Additionally at block 312, the AI assistant device 110 detects, via natural language processing, trigger words in the first utterances at the time 401, including the utterances 420*a* and 440*a*. For example, trigger words include words that may not indicate immediate distress or decline, but may be utilized over time to detect a change in a patient condition (including cognitive decline or depression, etc.). For example, patient 120 uses the word “okay” in utterance 420*a*. While the usage of the trigger word “okay” does not immediately indicate that the patient 120 is experiencing a condition change, the overuse of the trigger word may indicate a change in the future, as described herein. For examples, repeating a word frequently may indicate a loss of vocabulary, among other cognitive changes.

At block 314, the AI assistant device 110 determines a baseline level for the trigger word and tracks a number of uses of the trigger word using the model 405 at block 316. For example, the frequency of occurrence of trigger words in utterances in the environment 400 are tracked using the model 405 and used to determine a change in the patient condition as described in more detail in relation to FIGS. 5 and 6A-6C.

At block 318, the AI assistant device 110 adds the first utterances to the language tracking model, e.g., the language tracking model 405 shown in FIGS. 4A-D. For example, the utterances 420*a* and 440*a* are stored in the model 405. In some examples, the utterances include the answers to the conversation questions transmitted by the AI assistant device 110, so that the answers can be used to detect changes in the condition of the patient. In some examples, the model 405 also includes a tone detection engine, where a spoken tone or perceived tone of the utterances is also stored in the model 405. The tone may be determined from the voice intonation and/or the words spoken. For example, at time 401, the utterances 420*a*-440*a* include a positive or upbeat tone (based on audio tone recognition and natural language processing). The AI assistant device 110 also stores and/or updates a tracking of the tracked words (MW 450) and trigger words (TW 460) at the first time, time 401.

At block 320, the AI assistant device 110 determines whether the model 405 is trained to a level sufficient to monitor the patient 120 for a condition change. In some examples, the model 405 may be a pre-trained model such that after one collection of utterances, such as at time 401, the model 405 is sufficiently trained to monitor the patient 120 for condition changes. In another example, the AI assistant device 110 determines that the model requires additional training by comparing the trained data to one or more predefined thresholds for monitoring a patient and proceeds back to block 302 of method 300 to transmit conversation questions to the patient 120.

Figure 4B:
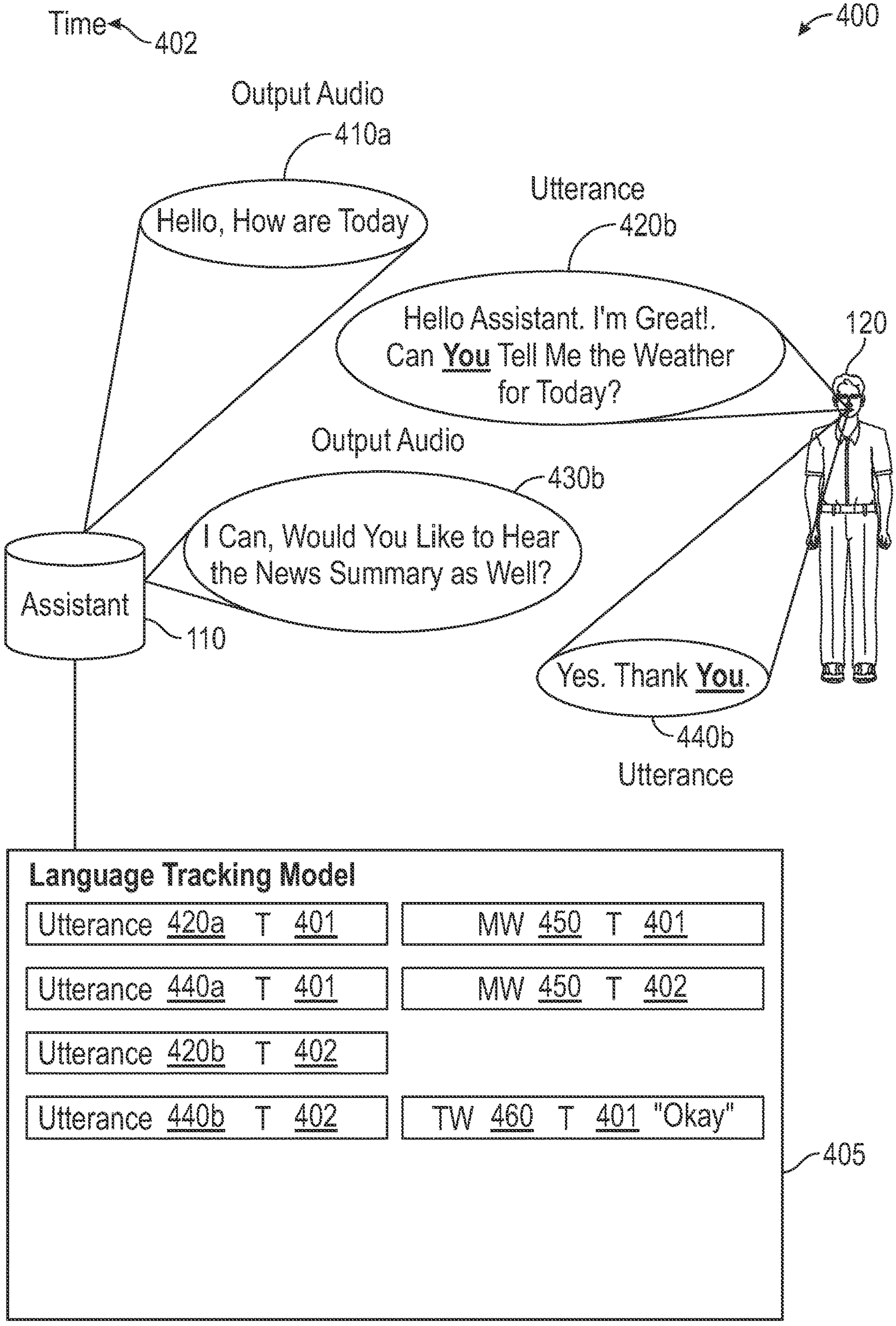

FIG. 4B illustrates a second time 402 where the AI assistant device 110 captures audio from the environment 400 which is used to build the model 405. As illustrated, the AI assistant device 110 outputs conversation questions including output audio 410*a*. The patient 120 responds to the AI assistant device 110 with utterance 420*b* which includes “Hello Assistant. I’m great! Can you tell me the weather for today?” and utterance 440*b* which includes “Yes. Thank you.” As described above, the AI assistant device 110 determines that the utterances 420*b* and 440*b* are spoken by the patient 120 and not background or environment noise such as environmental sounds 408 and performs the steps of blocks 304-318 of method 300. For example, the AI assistant device 110 tracks the usage of the tracked word “you” and adds the utterances 420*b*-440*b* to the model 405 with detect tone and time markings. At time 402, the patient 120 did not utter a trigger word, so the model 405 does not update the trigger word tracking. In some examples, the AI assistant device 110 returns to block 320 to determine whether the model requires additional training and proceeds back to block 302 of method 300 to transmit conversation questions to the patient 120.

Figure 4C:
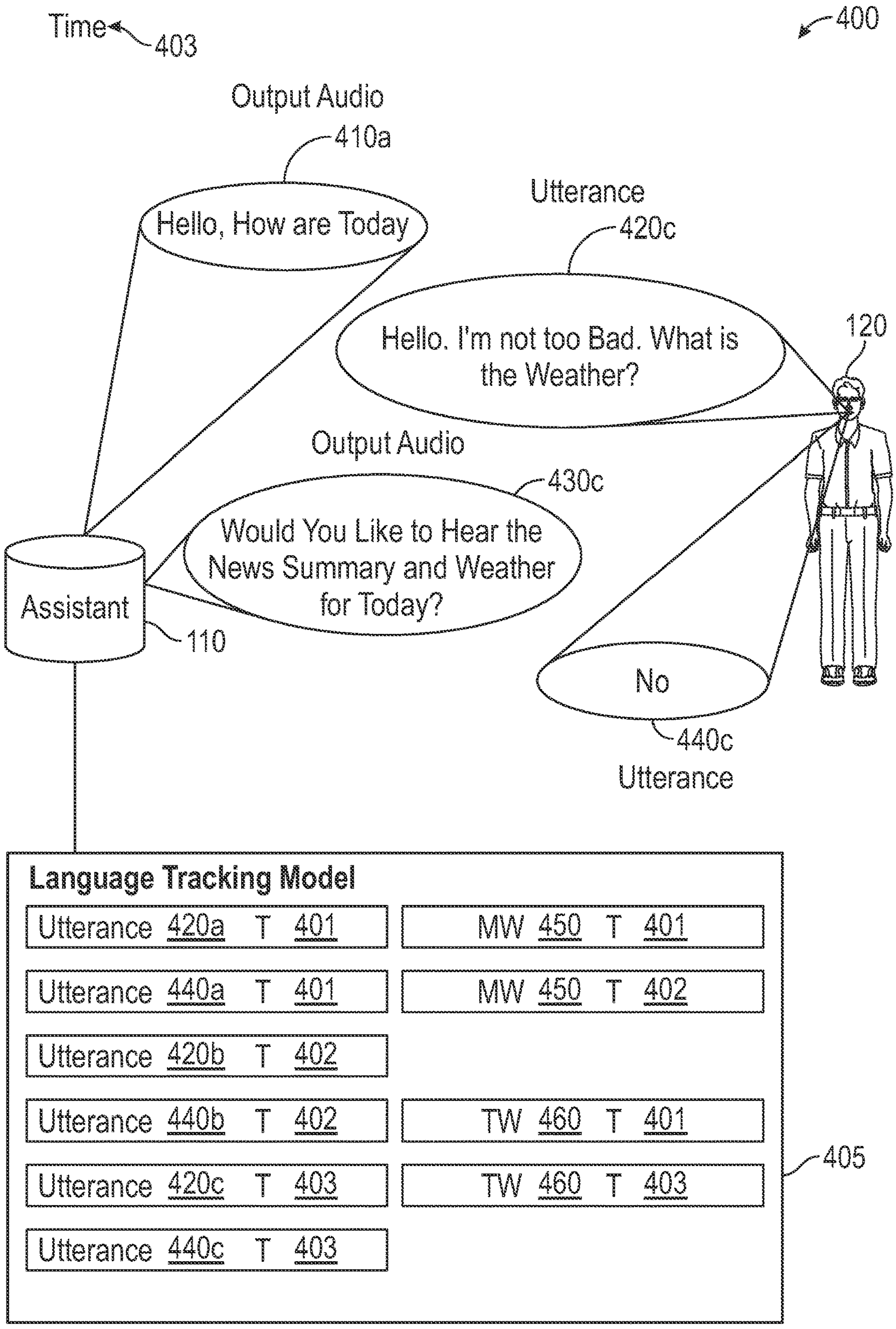

FIG. 4C illustrates a third time, time 403, where the AI assistant device 110 captures audio from the environment 400 which is used to build the model 405. As illustrated, the AI assistant device 110 outputs conversation questions including output audio 410*a*. The patient 120 responds to the AI assistant device 110 with utterance 420*c* which includes “Hello. I’m not too bad. What is the weather?” and utterance 440*a* which includes “No.” As described above, the AI assistant device 110 determines that the utterances 420*d* and 440*d* are spoken by the patient 120 and not background or environment noise such as environmental sounds 408 and performs the steps of blocks 304-318 of method 300. For example, the AI assistant device 110 adds the utterances 420*b*-440*b* to the model 405 with detected tone and time markings. At time 403, the patient 120 did not utter a tracked word or a trigger word, so the model 405 does not update the trigger word tracking. In some examples, the tone of the responses from the patient 120 varies across the times 401-403. For example, the patient 120 answers conversation questions with a short or agitated tone at time 403. The varying tones, as well as the varying answers among the times 401-403 allows for a sufficient level of training for the model 405 to provide monitoring of the patient 120.

In this example, method 300 proceeds to block 322 from block 320 and begins monitoring the patient 120 for condition changes using the model 405. In some examples, while the AI assistant device 110 is using the model 405 to monitor the patient 120 for condition changes, the AI assistant device 110 also continues training and updating the model 405. For example, the method 300 proceeds back to block 302 to transmit conversation questions to the patient 120.

Figure 4D:
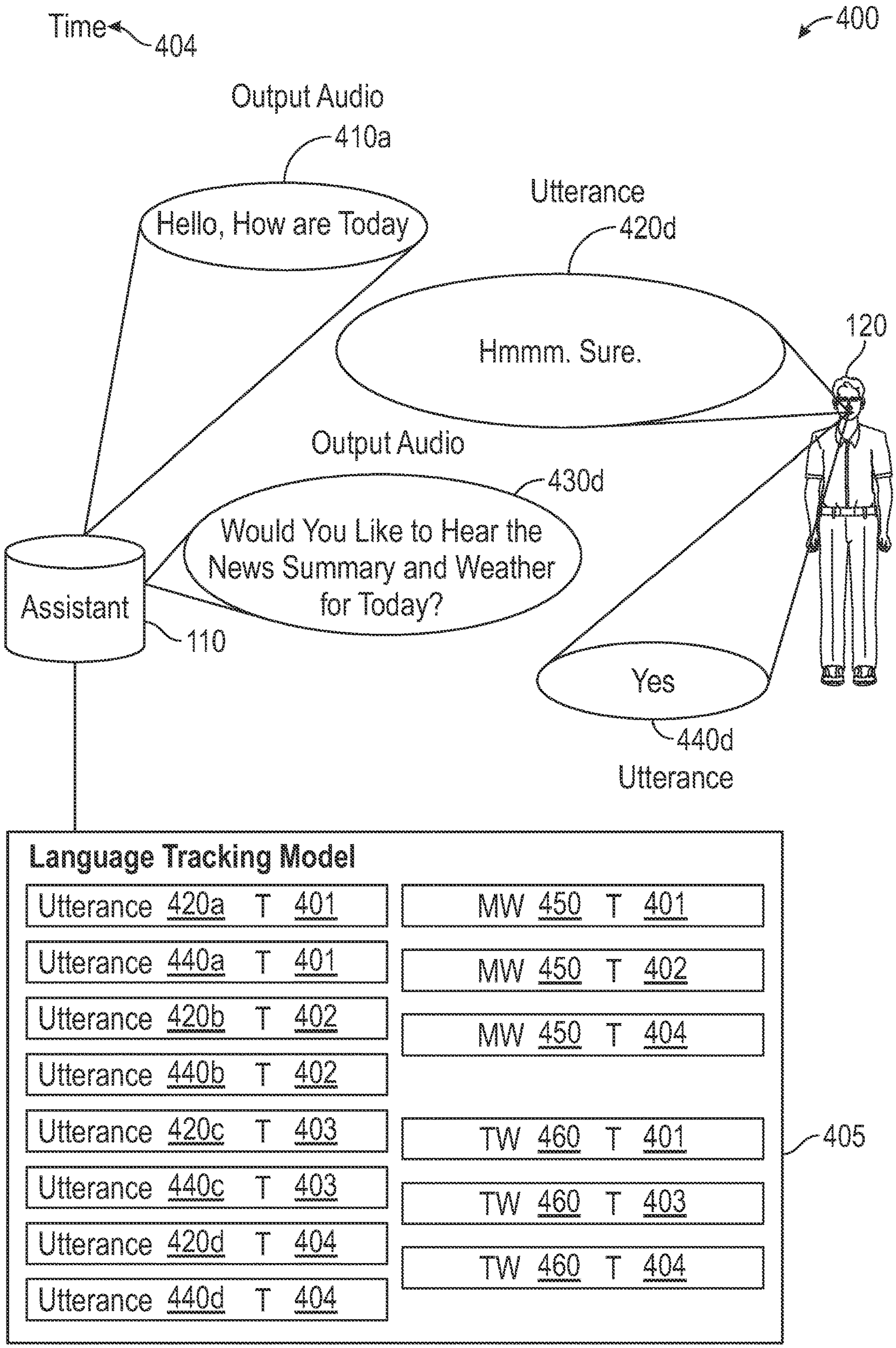

FIG. 4D illustrates a fourth time, time 404, where the AI assistant device 110 captures audio from the environment 400 to monitor the patient 120 and to train the model 405. As illustrated, the AI assistant device 110 outputs conversation questions including output audio 410*a*. The patient 120 responds to the AI assistant device 110 with utterance 420*d* which includes "Hmmm, sure?" and utterance 440*d* which includes "Yes." As described above, the AI assistant device 110 determines that the utterances 420*d* and 440*d* are spoken by the patient 120 and not background or environment noise such as environmental sounds 408 and performs the steps of blocks 304-318 of method 300. For example, the AI assistant device 110 adds the utterances 420*d*-440*d* to the model 405 with detected tone and time markings. At time 404, the AI assistant device 110 does not detect a condition change for the patient 120 and continues monitoring until a change is detected as described in relation to FIGS. 5 and 6A-6C.

Example Condition Change Scenarios

Figure 5:
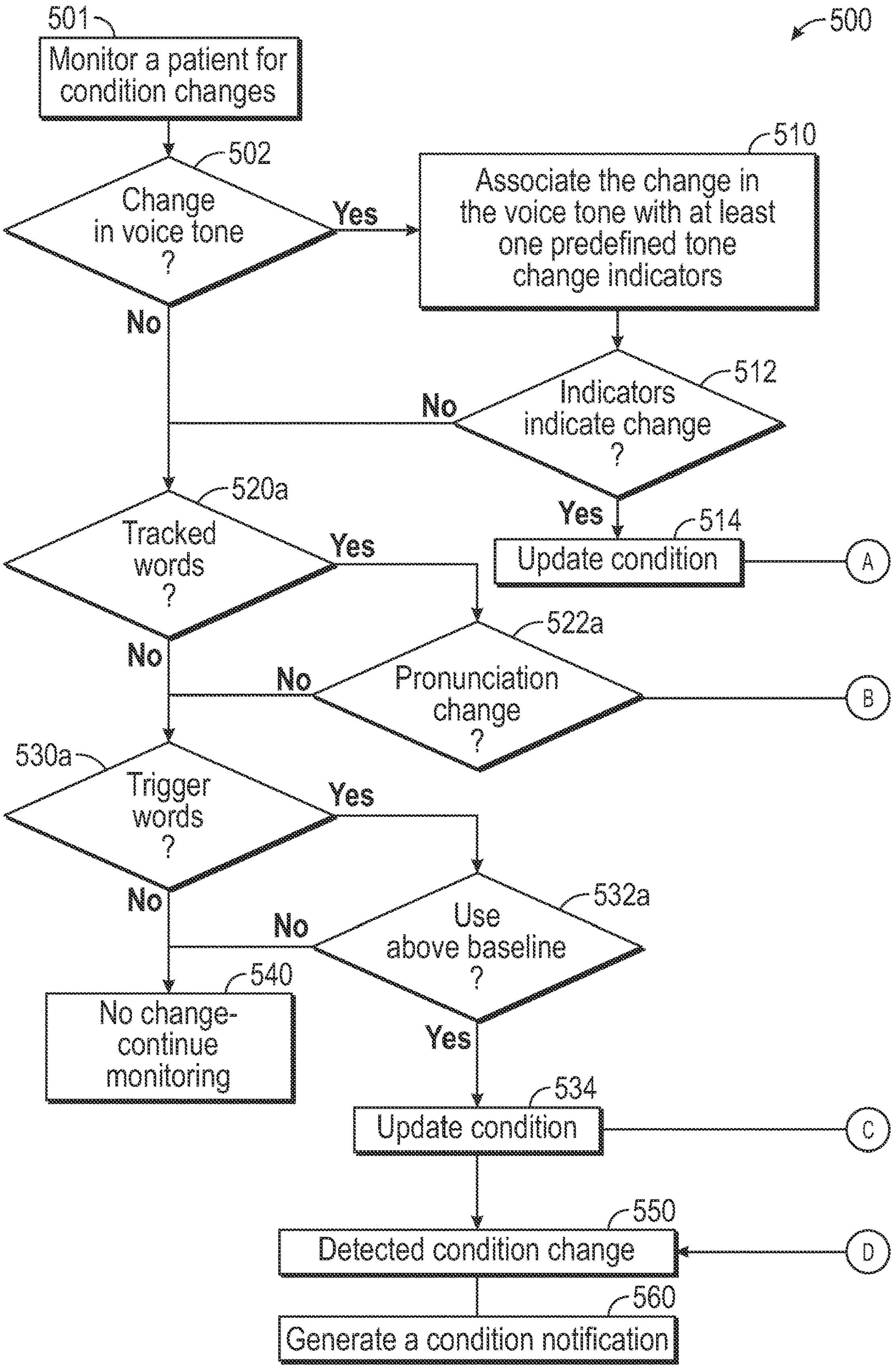
FIG. 5 is a flowchart of a method for detecting a condition change for a patient, according to embodiments of the present disclosure.
Figure 5:
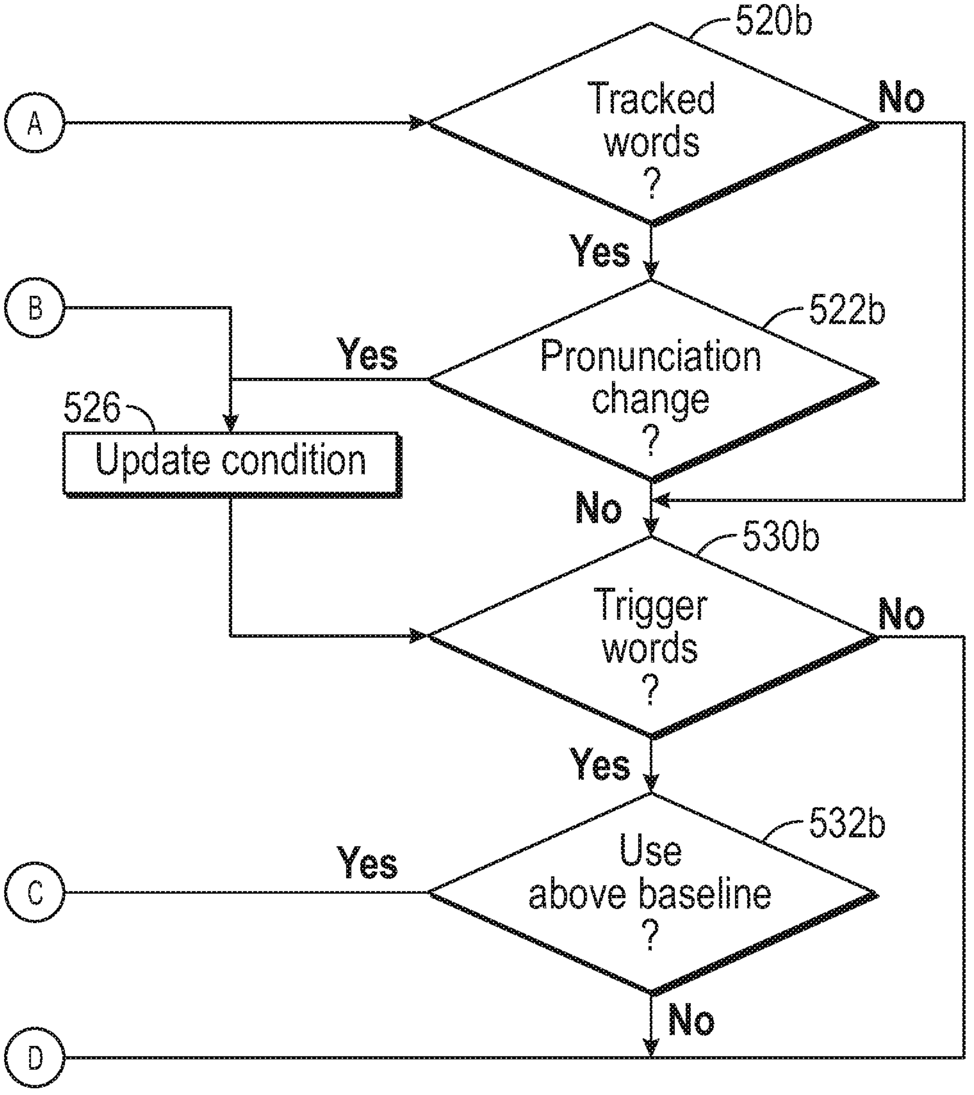

FIG. 5 is a flowchart of a method 500 for detecting a condition change for a patient, according to embodiments of the present disclosure. FIGS. 6A-6D illustrate example scenarios for how an AI assistant device may be used to detect a condition change for a patient, according to embodiments of the present disclosure. Various changes may be detected using speech patterns from the patient 120 and the trained ML model 405. For example, subtle change to mood, general cognition, and other health related changes are detected over a long time period using the language tracking model.

For ease of discussion, the steps of the method 500 will be discussed with reference to FIGS. 6A-C. As will be appreciated, the AI assistant device 110 in environment 400 in the scenarios 601-603 may perform specific functions requested by the patient (e.g., "tell me the weather") and call for assistance in response to receiving a command from a person in the environment 400 (e.g., "call an ambulance for me!"), and the commands issued to the AI assistant device 110 may be received from various patients, including patient 120, for themselves or from authorized person 130 on behalf of the patients 120.

Figure 6A:
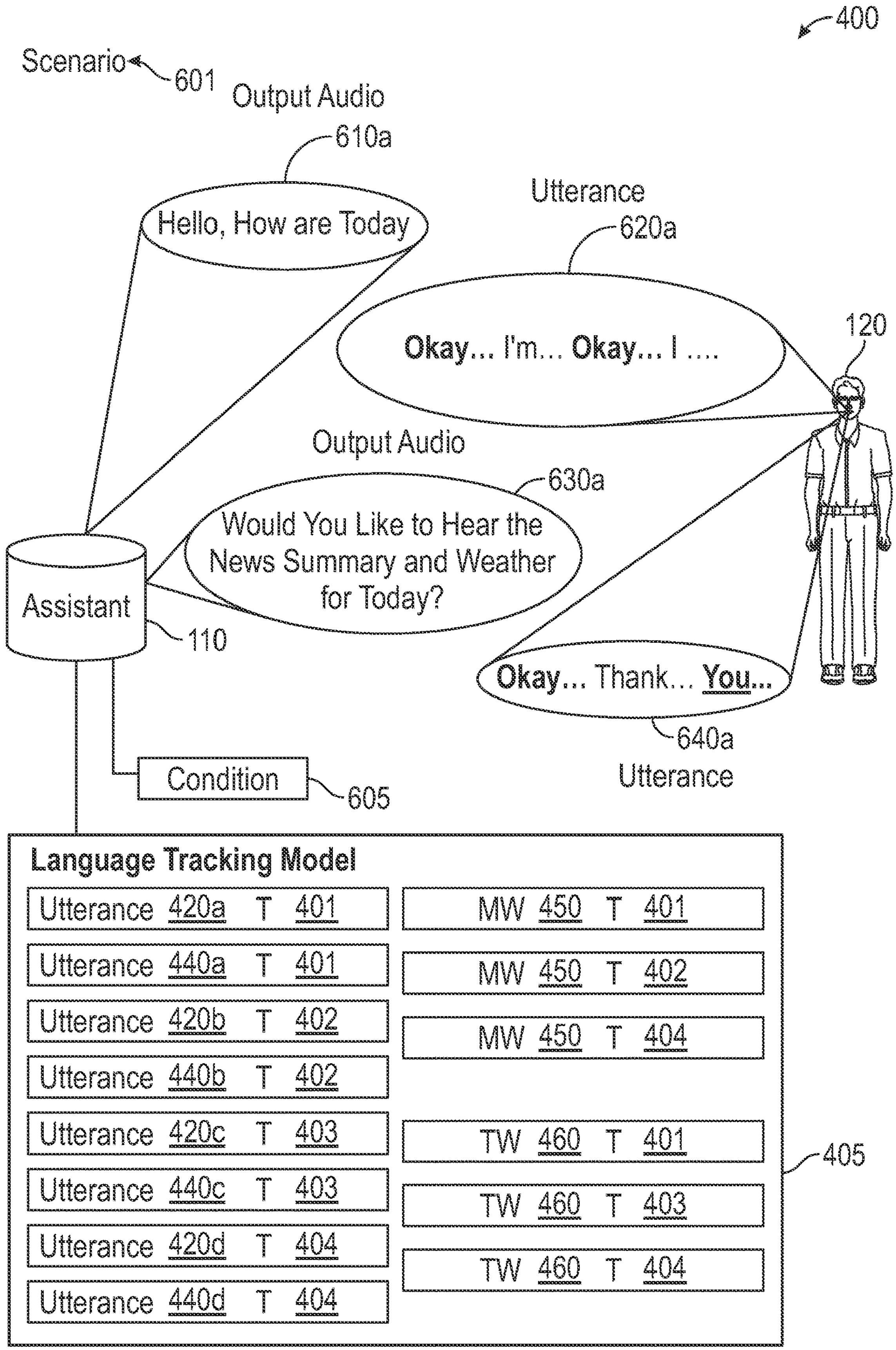
FIGS. 6A-6C illustrate example scenarios for how an AI assistant device may be used to detect a condition change for a patient, according to embodiments of the present disclosure.
Figure 6B:
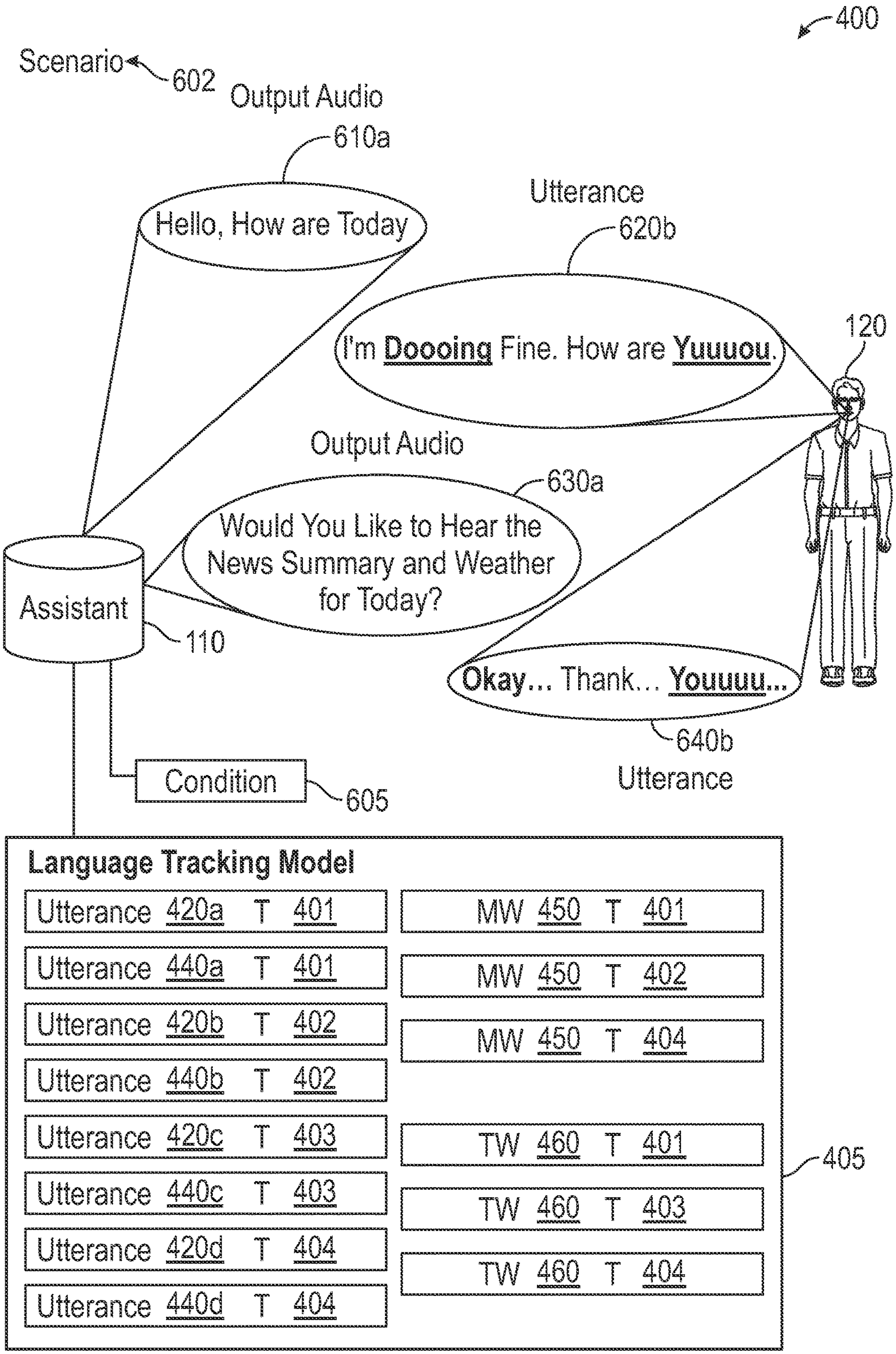
Figure 6C:
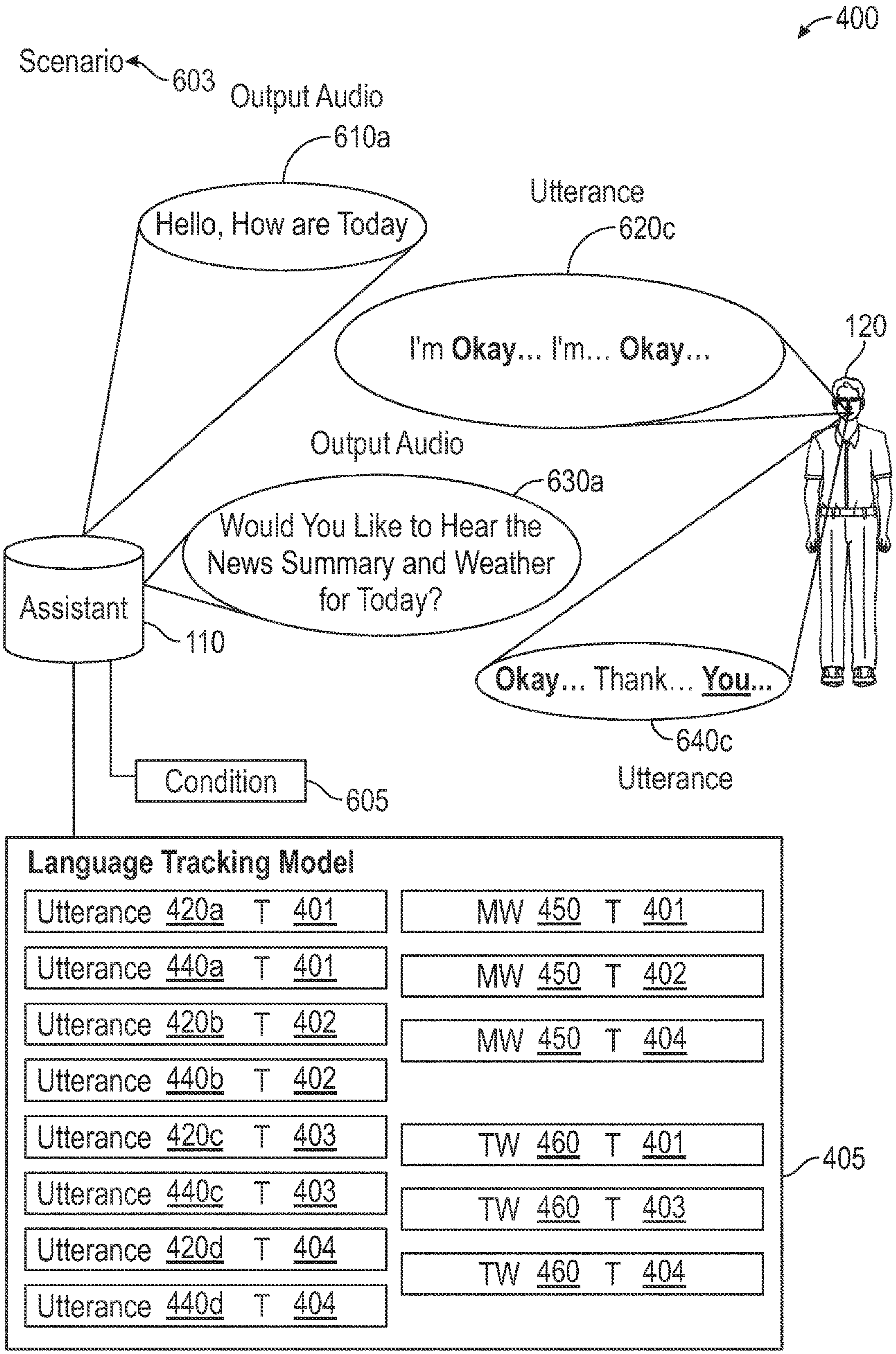

In each of FIGS. 6A-6C, the AI assistant device 110 is present in the environment 400 described in FIGS. 4A-4D and captures audio during a monitoring process. For example, as described in relation to block 322 of FIG. 3, the AI assistant device 110 monitors the patient 120 for condition changes. In some examples, a machine learning model provided by the AI assistant device 110 filters or divide the captured audio into two classes: speech sounds or utterances from the patient 120, such as utterances 620*a-n* and 640*a-n* in FIGS. 6A-6C and environmental sounds. The machine learning model may focus on certain frequency ranges based on demographic characteristics of the patient 120 that affect voice frequency (e.g., age, gender, smoking habits, pulmonary or vocal medical conditions) to identify a fundamental frequency (e.g., between 85 and 255 Hertz (Hz) for adults) and harmonics (e.g., between 30 and 3500 Hz for adults) therein to identify speech sounds. Frequency filtering is given as a non-limiting example for dividing captured audio into speech sounds and environmental sounds, but additional filtering is contemplated to identify environmental sounds within the frequency range of human speech and elements of human speech outside of the main ranges used for speech.

The AI assistant device 110 provides an audio recognition engine, which may be another machine learning model or an additional layer of the filtering machine learning model, that builds or otherwise trains a language learning model, such as model 405 which is trained as described in relation to FIGS. 3 and 4A-4D. In some examples, the AI assistant device 110 uses the model 405 and conversation questions to monitor the patient 120. For example, the conversation questions may include the same or similar greetings and service offerings which elicited a response from the patient 120 while the model 405 was trained. The conversation questions can be the same during each scenario or times shown in FIGS. 4A-4D and 6A-6C. For example, audio outputs 610*a-c* are a standard greeting such as "hello, how are you today?" The audio output 610*a* and other audio outputs 630*a-d* may vary based on responses from patient 120 the time of day, season, etc., where the AI assistant device 110 using AI models determines and generates the various audio outputs.

In addition to processing and classifying the environmental sounds to and listening for answers to conversation questions/output audio, in some embodiments, the audio recognition engine may include speech recognition for various key phrases. For example, various preloaded phrases may be preloaded for local identification by the AI assistant device 110, such as, a name of the AI assistant to activate the AI assistant device 110 (e.g., "Hey, ASSISTANT") or phrases to deactivate the AI assistant device 110 (e.g., "never mind", "I'm fine", "cancel request", etc.). The AI assistant device 110 may offload further processing of speech sounds to a speech recognition system offered by remote computing resources 160 to identify the contents and intents of the various utterances from the patient 120 captured in the environment 400 during the scenarios 601-603.

Referring to back to FIG. 5, the method 500 begins at block 501 where the AI assistant device 110 monitors the patient 120 for condition changes. In some examples, monitoring the condition changes includes capturing, via the AI assistant device 110, second audio from the environment and detecting second utterances from the second audio for the patient 120. In some examples, the AI assistant device 110 transmits the conversation questions at regular time intervals in order to monitor the condition of the patient 120 as compared to a baseline or initial condition for the patient 120 using the model 405.

FIG. 6A illustrates a first scenario where the AI assistant device 110 detects a condition change for a patient 120 using the model 405. As illustrated, the AI assistant device 110 outputs conversation questions including output audio 610*a*. The patient 120 responds to the AI assistant device 110 with utterance 620*a* which includes "Okay . . . I'm . . . okay . . . I . . . ." and utterance 640*a* which includes "okay . . . thank . . . you . . . ." As described above, the AI assistant device 110 determines that the utterances 620*a* and 640*a* are spoken by the patient 120 and not background or environment noise such as environmental sounds 408.

At block 502, the AI assistant device 110, using the model 405 and a language tracking engine, detects via audio associated with utterances stored in the language tracking model, such as model 405, a change in voice tone of the patient. At block 510, the AI assistant device 110 associates the change in the voice tone with at least one predefined tone change indicators and determines, from the at least one predefined tone change indicators, a change in the condition of the patient. For example, utterance 620*a* and 640*a* in scenario 601 may include an aggressive and loud voice tone as detected by the AI assistant device 110.

The AI assistant device 110, using the model 405 associates aggressive and loud voice tones with an agitation indicator. An increase in the agitation indicator of the tone of the patient 120 may indicate symptoms of cognitive decline caused by memory loss conditions, cognitive decline caused by minor strokes, other neurological events, or other conditions such as depression or anxiety, among others. In some examples, the indicator indicates a change in the tone as determined at block 512 and the AI assistant device 110 updates a condition 605 of the patient 120 at block 514.

The condition 605 may also be updated using additional learning model methods as described in relation to blocks 520*a*-550. For example, a condition change from just a detected tone change may warrant a note for follow up or an update to the model 405, while a tone change along with other detected changes in the speech patterns may warrant a more immediate follow up or alert as described herein.

In some examples, at block 512, the AI assistant device 110 determines that the tone indicators do not indicate a change in the condition of the patient 120 and the method 500 proceeds to block 520*a*. For example, the tone of the utterances 620*a* and 640*a* may indicate agitation, but may be within an expected range as determined by the language engine of the AI assistant device 110 and the model 405.

In both examples, whether the AI assistant device 110 has determined there is a change associated with the tone of the patient or not, the AI assistant device 110 continues to check other factors such as at blocks 520*a* and 520*b* of method 500, where the AI assistant device 110 detects the presences of tracked words. In the scenario 601, there are tracked words in the utterances 620*a* and 620*b* (i.e., "you"). For the scenario 601, at block 522*b* the AI assistant device 110 detects, via natural language processing and fuzzy matching processing, that a pronunciation of the tracked words has not changed in the utterances 620*a* and 640*a*.

In another example, FIG. 6B illustrates a second scenario 602 where the AI assistant device 110 detects a condition change for a patient 120 using the model 405. As illustrated, the AI assistant device 110 outputs conversation questions including output audio 610*a*. The patient 120 responds to the AI assistant device 110 with utterance 620*b* which includes "I'm doooing fine. How are yuuuou." and utterance 640*b* which includes "okay . . . thank . . . youuuu . . . ." In this example, the patient 120 is pronouncing tracked word "you" with a long pause. In some examples, the word may not be readily intelligible. For example, when the patient 120 is pronouncing a word with significant alteration, the AI assistant device 110 detects, via natural language processing and fuzzy matching processing, that the word is a tracked word and that the pronunciation has changed.

Additionally, the AI assistant device 110 may detect via natural language processing and fuzzy matching processing additional words that may have altered pronunciation. For example, "doing" is not a tracked word in the model 405, but the AI assistant device 110 uses the natural language processing and fuzzy matching processing to determine that the word the patient is pronouncing is "doing" and that the pronunciation is unexpected for the word and or the patient 120.

When the AI assistant device 110 detects a change in pronunciation or unexpected pronunciation for words including tracked and non-tracked words (at either block 522*a* or block 522*b*), the AI assistant device 110 updates the patient's condition 605 at block 534. In another example, the AI assistant device 110 does not detect a pronunciation change and the method 500 proceeds to block 530*b* from 522*b* (e.g., in scenario 601). In an example, where no tone change is detected and no pronunciation change is detected, the method 500 proceeds to block 530*a*.

At blocks 530*a* and 530*b*, the AI assistant device 110 determines whether trigger words are present in the second utterances. In an example, where trigger words are present, the AI assistant device 110 compares the number of uses to the baseline level and predefined threshold for the trigger word. For example, in the scenario 601, there are trigger words in the utterances 620*a* and 620*b* (i.e., okay). At block 532*b* the AI assistant device 110 determines that the usage of the trigger word in scenario 601 is below a baseline according to the model 405.

In another example, FIG. 6C illustrates a third scenario 603 where the AI assistant device 110 detects a condition change for a patient 120 using the model 405. As illustrated, the AI assistant device 110 outputs conversation questions including output audio 610*a*. The patient 120 responds to the AI assistant device 110 with utterance 620*c* which includes "I'm Okay . . . I'm . . . okay . . . ." and utterance 640*c* which includes "okay . . . thank . . . you . . . " In this example, the patient 120 is repeating the trigger word, which can indicate a mood or other condition change. For example, repeated trigger words may indicate depression or a change in vocabulary caused by minor strokes etc.

When the AI assistant device 110 detects a usage of trigger words above a respective baseline (at either block 532*a* or block 532*b*), the AI assistant device 110 updates condition 605 at block 534. In another example, the AI assistant device 110 does not detect a usage above a baseline and the method 500 proceeds to block 550 from 532*b* or to block 540 from block 532*a*. In some examples, none of the indicators in the model 405 indicate that the condition 605 of the patient 120 has changed.

In an example where one or more indicators has caused an update to the condition 605, the AI assistant device 110 detects/determines the condition change from the condition 605. For example, the AI assistant device 110 aggregates the changes made in blocks 501-534 of method 500. In some examples, the AI assistant device 110 may also detect via a language tracking engine provided by the AI assistant device 110 and the model 405 additional factors/indicators for a condition change. For example, slurring or stuttering speech, slowed/paused speech, and other factors derived from the model 405 and the utterances in the scenarios 601-603 may further indicate a condition change.

At block 560, the AI assistant device 110 generates a condition notification comprising the condition change indicating a condition of the patient has changed from the first time to the second time. Generation of the condition notification is further described in relation to FIGS. 7 and 8A-8B.

Example Condition Notification Scenarios

Figure 7:
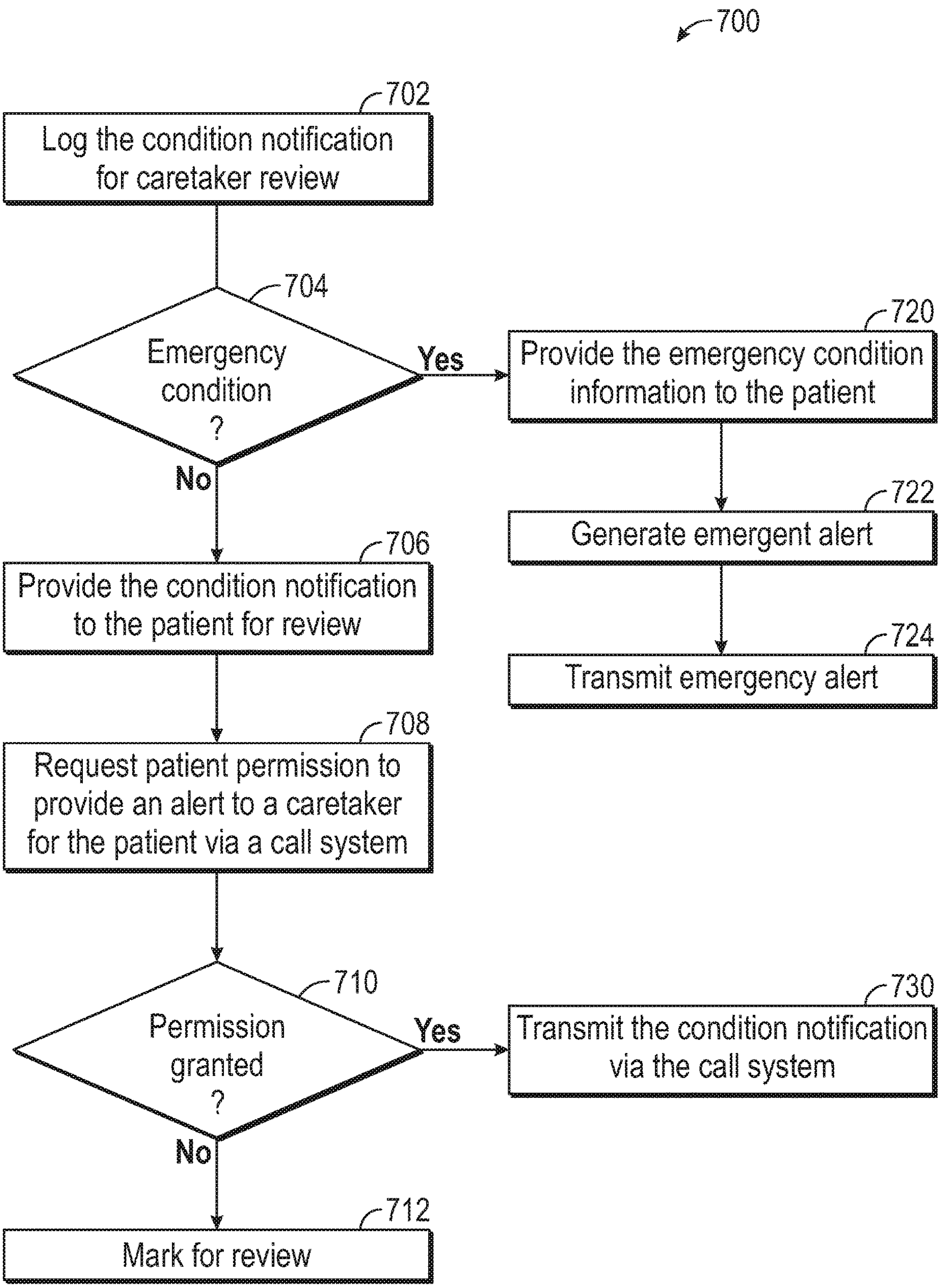
FIG. 7 is a flowchart of a method for a condition notification, according to embodiments of the present disclosure.
Figure 8A:
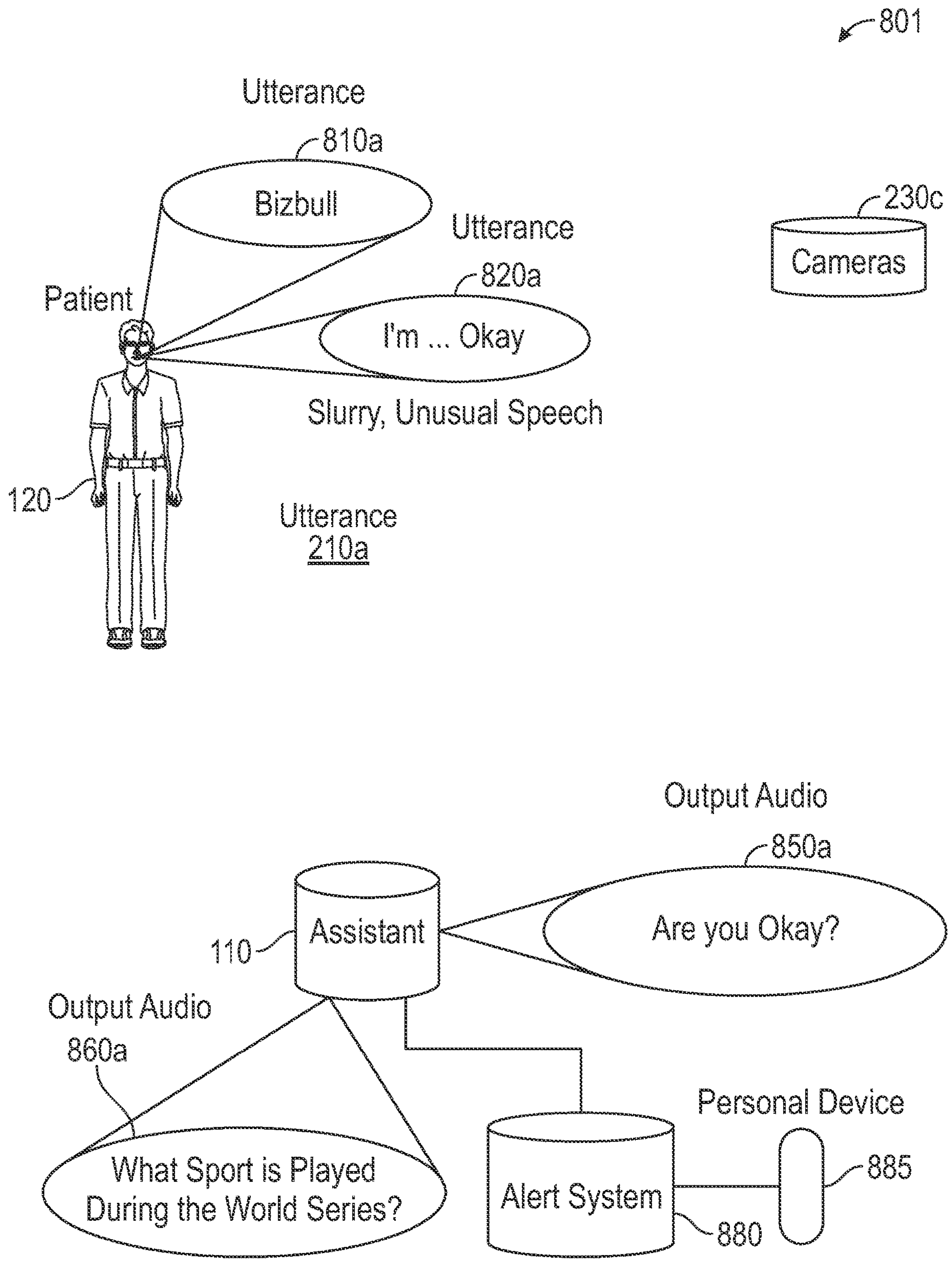
FIGS. 8A-8B illustrates an example scenario when an AI assistant device passively calls for assistance, according to embodiments of the present disclosure.
Figure 8B:
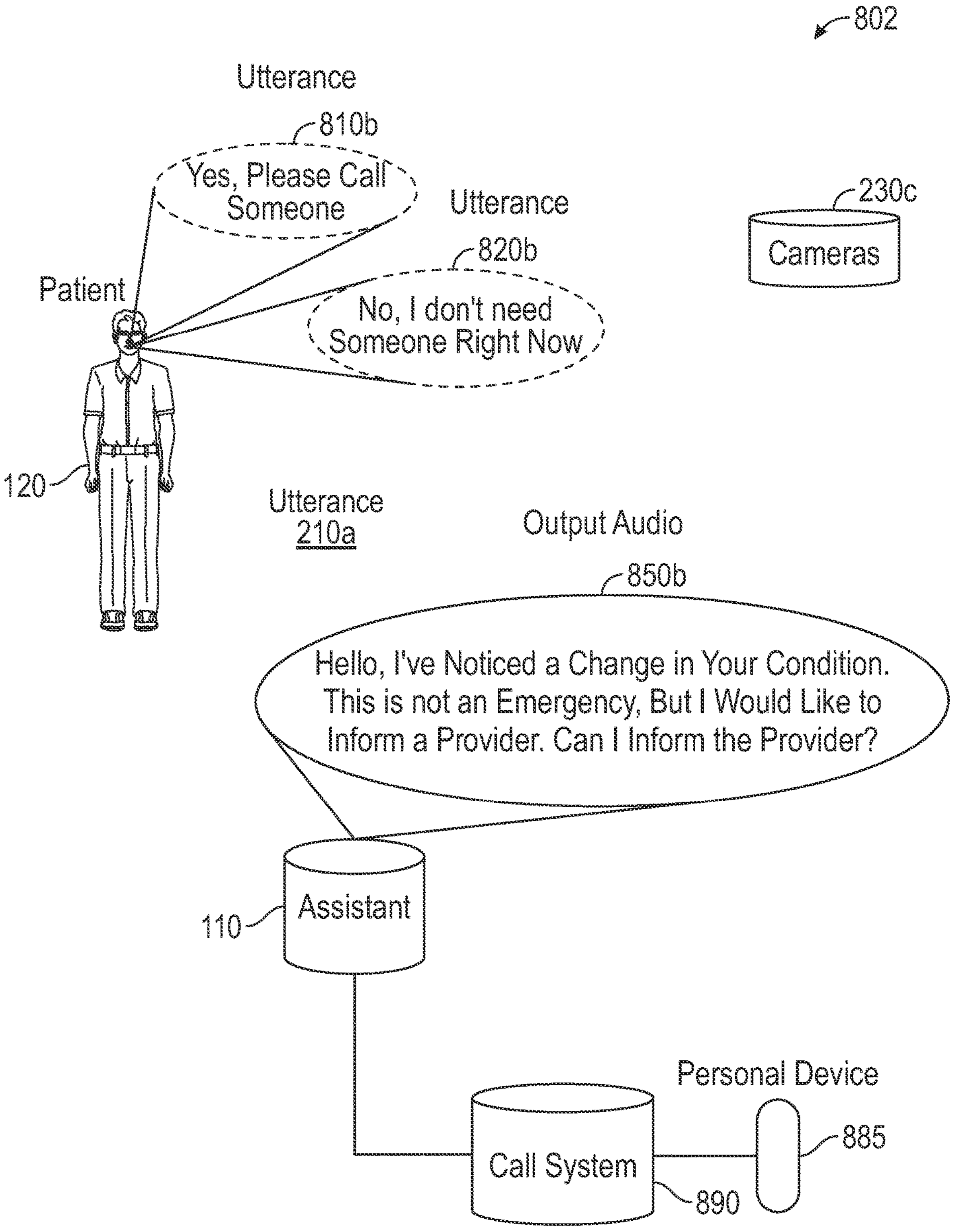

FIG. 7 is a flowchart of a method 700 for a condition notification, according to embodiments of the present disclosure. FIGS. 8A-8B illustrates an example scenario when an AI assistant device passively calls for assistance, according to embodiments of the present disclosure. For ease of discussion, the steps of the method 700 will be discussed with reference to FIGS. 8A-8B.

Method 700 begins at block 702 where the device 110 logs the condition notification for caretaker review. In some examples, the condition notification includes a minor change that does not warrant immediate follow up. For example, a detected change in the memory of the patient 120 may not require an immediate visit from a provider. In another example, the condition notification includes a significant or sudden change in the speech patterns, which requires attention as soon as feasible.

At block 704, the device 110 determining, from the condition change, whether an emergency condition change is indicated. In some examples, the device 110 may conduct further inquiries into the condition of the patient 120 to determine if a medical emergency is occurring, as described in FIG. 8A. At block 720, the AI assistant device 110 provides emergency condition information to the patient via the AI assistant and generates an emergency alert via an alert system associated with the AI assistant at block 722. At block 724, the device 110 transmits the emergency alert via an alert system. In some examples, the alert system is a phone network and the emergency alert is sent to a personal device associated with a caretaker for the patient as at least one of a text message or a phone call using a synthesized voice. In another example, the call system is part of an alert system in a group home or medical facility, the call system transmits the emergency alert via a broadcast message to a plurality of personal devices associated with caretakers in the group home or medical facility.

FIG. 8A illustrates an example scenario 801 where an AI assistant device 110 determines that the condition change is an emergency condition or emergency. For example, the device 110 identifies that a patient 120 is experiencing a stroke, according to embodiments of the present disclosure. Additionally or alternatively to monitoring a patient 120 via audio inputs from the patient 120 and the environment 400. In some examples, the AI assistant device 110 detects a condition change as described in relation to FIGS. 5 and 6A-6C and follows up with the patient 120 to determine and urgency of addressing the condition change. For example, while small changes in speech detected by the AI assistant device 110 using the model 405 may indicate that a follow up with a medical professional is needed. Other more dramatic changes may indicate that a medical emergency, such as a heart attack, a major stroke, etc. is occurring.

For example, two of the signs for rapid diagnosis of strokes in patients 120 include slurred or disjointed speech (generally, slurred or slurry speech) and facial paralysis, often on only one side of the face, causing "facial droop", where an expression is present on one side of the face and muscle control has been lost in the lower face and one side of the upper face. Depending on the severity of the stroke in the patient 120, the patient 120 may no longer be able to produce intelligible speech or otherwise actively call for assistance. Accordingly, the AI assistant device 110 may analyze utterances 810*a* and 820*a* generated by the patient 120 to determine when to generate an alert for a medical professional to diagnose and aid the patient 120.

As illustrated in FIG. 8A, the AI assistant device 110 has determined that the condition has changes and transmits audio output 850*a* to the patient 120. Unlike other devices that remain inactive until a cue phrase is clearly received, the AI assistant device 110 operating according to the present disclosure may continuously monitor the environment 400 for human speech and environmental sounds that would otherwise be discarded or ignored. Using these discarded sounds, an audio recognition engine provided by the AI assistant device 110 may look for "near misses" for known samples of speech to identify slurring.

For example, the first portion of the first utterance 210*a* of "Hey assitsn" may be compared to the cue phrase of "Hey Assistant" to determine that the uttered speech does not satisfy a confirmation threshold for the patient 120 to have spoken "Hey ASSISTANT" to activate the AI assistant device 110, but does satisfy a proximity threshold as being close to intelligibly saying "Hey ASSISTANT". When the confidence in matching a received phrase to a known phrase falls between the proximity threshold (as a lower bound) and the confirmation threshold (as an upper bound), and does not satisfy a confirmation threshold for another known phrase (e.g., "Hey hon" to address a loved one as 'hon'), the AI assistant device 110 may take further action to determine if the patient is in distress.

When the patient 120 is identified as being in distress as possibly suffering a stroke (i.e., an emergency condition), the AI assistant device 110 may generate audio outputs 850*a* and 860*a* to prompt the patient 120 to provide further utterances to gather additional speech samples to compare against the model 405 to guard against accents or preexisting speech impediments yielding false positives for detecting a potential stroke.

As illustrated in FIG. 8A, the AI assistant device 110 issues an audio output 850*a* of "are you okay" to prompt the patient 120 to respond. The patient 120 responds via a second utterance 820*a* of "I'm . . . okay", which the audio recognition engine may compare against a previously supplied utterance of "I'm okay" from the patient 120 to identify that a pause between "I'm" and "okay" in the second utterance 820*a* may be indicative of speech difficulties or slurring.

The AI assistant device 110 may generate a second audio output 860*a* of "What sport is played during the World Series?" or another pre-arranged question/response pair that the patient 120 should remember the response to. The second audio output 860*a* prompts the patient 120 to reply via an utterance 810*a*, "Bizbull" to convey the answer of "baseball", albeit with a slurred speech pattern. Similarly, if the patient 120 were to supply an incorrect answer (e.g., basketball) after having established knowledge of the correct answer when setting up the pre-arranged question/response, the mismatch may indicate cognitive impair, even if the speech is not otherwise slurred, which may be another sign of stroke.

When the AI assistant device 110 detects slurred speech via the utterances 210 almost (but not quite) matching known audio cues or not matching a pre-supplied audio clip of the patient 120 speaking the words from model 405, the AI assistant device 110 may activate various supplemental sensors to further identify whether the patient is in distress. For example, a camera sensor 230*c* of the sensors 230 may be activated and the images provided to a facial recognition system (e.g., provided by remote computing resources 160) to identify whether the patient 120 is experiencing partial facial paralysis; another sign of stroke.

Additionally or alternatively, the AI assistant device 110 may the access the electronic health records 180 for the patient 120 to adjust the thresholds used to determine whether the slurred speech or facial paralysis is indicative of stroke. For example, when a patient 120 is observed with slurred speech, but the electronic health records 180 indicate that the patient 120 was scheduled for a dental cavity filling earlier in the day, the AI assistant device 110 may adjust the confidence window upward so that false positives for stroke are not generated due to the facial droop and speech impairment expected from local oral anesthesia. In another example, when the patient 120 is prescribed medications that affect motor control, the AI assistant device 110 may adjust the confidence window upward so that greater confidence in stroke is required before an alert is generated. In a further example, when the electronic health records 180 indicate that the patient 120 is at an elevated risk for stroke (e.g., due to medications, previous strokes, etc.), the AI assistant device 110 may adjust the confidence window downward so that lower confidence in stroke is required before an alert is generated.

When the patient 120 has slurred speech and/or exhibits partial facial paralysis sufficient to satisfy the thresholds for stroke, the AI assistant device 110 determines that the patient 120 is in distress and is non-responsive (despite potentially attempting to be responsive), and therefore generates an alert that the patient 120 is in distress.

In various embodiments, the AI assistant device 110 transmits the alert to an emergency alert system, alert system 880, to propagate according to various transmission protocols to one or more personal devices 885 associated with authorized person 130 to assist the patient 120. Example hardware as may be used in the alert system 880 and the personal devices 885 can include a computing system 900 as is discussed in greater detail in FIG. 9. In some embodiments, the alert system 880 is connected to a telephone network and pushes the alerts as one or more individual messages sent to a corresponding one or more personal devices of the personal devices 885 that are cellphones or pagers via text messages (e.g., via Short Message Service (SMS) or Multimedia Message Service (MMS)) or phone calls using a synthesized voice to alert the authorized person 130 that the patient 120 is in distress. Additionally or alternatively, when the alert system is part of an alert system in a group home or medical facility, the call system 890 can transmit the alert via a broadcast message to be received by a plurality of personal devices 885 associated with caretakers (e.g., authorized person 130) in the group home or medical facility.

Returning back to method 700 of FIG. 7, at block 706, when the condition change is not an emergency, the AI assistant device 110 provides the condition notification to the patient for review. At block 708, the AI assistant device 110 requests patient permission to provide an alert to a caretaker for the patient via a call system. At block 710, the AI assistant device 110 determines whether permission was granted by the patient. When the AI assistant device 110 receives the patient permission from the patient to provide the alert to the caretaker, the AI assistant device 110 transmits the condition notification via the call system at block 730. In some examples, the call system transmits the condition notification via a phone network to a personal device associated with the caretaker for the patient as at least one of: a text message, or a phone call using a synthesized voice.

FIG. 8B illustrates an example scenario 802 where an AI assistant device 110 determines that the condition change is not an emergency condition or emergency. For example, the device identifies that a patient 120 has experienced a condition change, but the change does not require immediate/urgent medical attention. In contrast to the emergency conditions discussed in scenario 801, non-emergency conditions can be addressed in a less urgent manner. For example, a change overall attitude or mood of the patient 120 may be followed up by a medical professional several hours or days after the condition change is detected. In another example, detected change in memory (e.g., memory loss) may be followed up by medical professional on a shorter time scale than change in mood, but not on an emergency level. Additionally, minor strokes may have caused the detected change in the condition of the patient 120 and may require an immediate, but non-emergency follow up with a medical professional. In each of these examples, the AI assistant device 110 interacts with the patient 120 in order to determine how the patient would like to handle the detected condition change and provider notification.

For example, the AI assistant device 110 outputs the output audio 850*b* which states "Hello, I've noticed a change in your condition. This is not an emergency, but I would like to inform a provider. Can I inform the provider?" The patient 120 in turn may respond via utterance 810*b* granting permission to call a provider or respond via utterance 820*b* declining a call.

In some examples, the AI assistant device 110 may inform the patient 120 of the details of the detected change. For example, the AI assistant device 110 may inform the patient 120 that their speech indicates a high agitation level. In this example, the patient 120 may know that they are agitated for a specific reason (not related to a condition change) and decline the call from the AI assistant device 110. In this example, the AI assistant device 110 determines that the condition change may be followed up at a later time and does not transmit a call to a provider.

In another example, the AI assistant device 110 informs the patient 120 that a condition change indicates that minor strokes may have occurred. In this example, whether the patient declines the call or grants permission for the call, the AI assistant device 110 determines that the condition change requires provider notification notifies at least one provider.

In various embodiments, the AI assistant device 110 transmits a condition notification to a call system 890 to propagate according to various transmission protocols to one or more personal devices 885 associated with authorized person 130 to assist the patient 120. The call system 890 provides a lower importance call level compared to the alert system 880. Example hardware as may be used in the system 890 and the personal devices 885 can include a computing system 900 as is discussed in greater detail in FIG. 9. In some embodiments, the call system 890 is connected to a telephone network and pushes the alerts as one or more individual messages sent to a corresponding one or more personal devices of the personal devices 885 that are cellphones or pagers via text messages (e.g., via Short Message Service (SMS) or Multimedia Message Service (MMS)) or phone calls using a synthesized voice to alert the authorized person 130 that the patient 120 needs a follow-up visit to address the condition change. Additionally or alternatively, when the call system 890 is part of an alert system in a group home or medical facility, the call system 890 can transmit the condition notification via a broadcast message to be received by a plurality of personal devices 885 associated with caretakers (e.g., authorized person 130) in the group home or medical facility.

Example Computing Hardware

Figure 9:
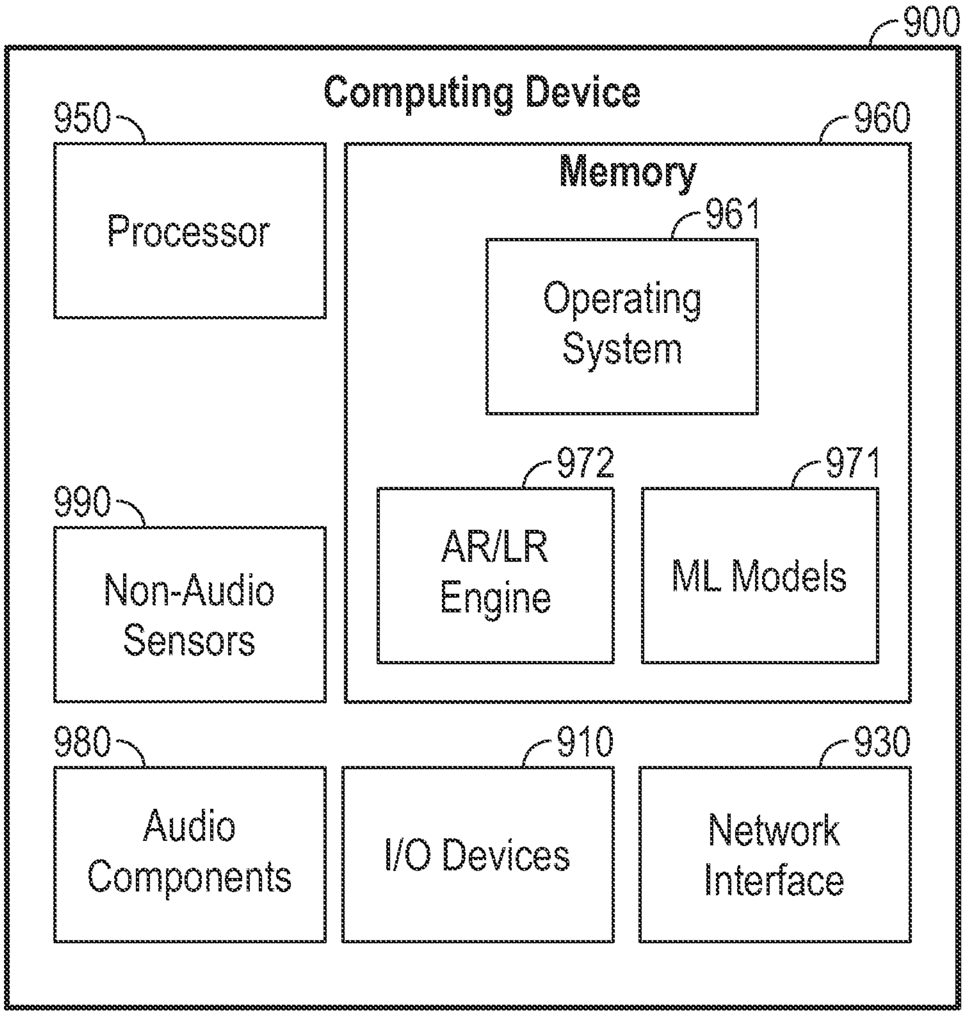
FIG. 9 illustrates a computing system, according to embodiments of the present disclosure.

FIG. 9 illustrates a computing system 900, which may be the AI assistant device 110, a personal device 330 (e.g., a computer, a laptop, a tablet, a smartphone, etc.), or any other computing device described in the present disclosure. As shown, the computing system 900 includes, without limitation, a processor 950 (e.g., a central processing unit (CPU)), a network interface 930, and memory 960. The computing system 900 may also include an input/output (I/O) device interface connecting I/O devices 910 (e.g., keyboard, display and mouse devices) to the computing system 900.

The processor 950 retrieves and executes programming instructions stored in the memory 960. Similarly, the processor 950 stores and retrieves application data residing in the memory 960. An interconnect can facility transmission, such as of programming instructions and application data, between the processor 950, I/O devices 910, network interface 930, and memory 960. The processor 950 is included to be representative of a single processor, multiple processors, a single processor having multiple processing cores, and the like. And the memory 960 is generally included to be representative of a random access memory. The memory 960 can also be a disk drive storage device. Although shown as a single unit, the memory 960 may be a combination of fixed and/or removable storage devices, such as magnetic disk drives, flash drives, removable memory cards or optical storage, network attached storage (NAS), or a storage area-network (SAN). The memory 960 may include both local storage devices and remote storage devices accessible via the network interface 930. One or more machine learning models 971 may be are maintained in the memory 960 to provide localized portion of an AI assistant via the computing system 900. Additionally, one or more AR engines 972 may be maintained in the memory 960 to match identified audio to known events occurring in an environment where the computing system 900 is located.

Further, the computing system 900 is included to be representative of a physical computing system as well as virtual machine instances hosted on a set of underlying physical computing systems. Further still, although shown as a single computing system, one of ordinary skill in the art will recognize that the components of the computing system 900 shown in FIG. 9 may be distributed across multiple computing systems connected by a data communications network.

As shown, the memory 960 includes an operating system 961. The operating system 961 may facilitate receiving input from and providing output to audio components 980 and non-audio sensors 990. In various embodiments, the audio components 980 include one or more microphones (including directional microphone arrays) to monitor the environment for various audio including human speech and non-speech sounds, and one or more speakers to provide simulated human speech to interact with persons in the environment. The non-audio sensors 990 may include sensors operated by one or more different computing systems, such as, for example, presence sensors, motion sensors, cameras, pressure or weight sensors, light sensors, humidity sensors, temperature sensors, and the like, which may be provided as separate devices in communication with the AI assistant device 110, or a managed constellation of sensors (e.g., as part of a home security system in communication with the AI assistant device 110). Although illustrated as external to the computing system 900, and connected via an I/O interface, in various embodiments, some or all of the audio components 980 and non-audio sensors 990 may be connected to the computing system 900 via the network interface 930, or incorporated in the computing system 900.

Additional Considerations

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word “exemplary” means “serving as an example, instance, or illustration.” Any aspect described herein as “exemplary” is not necessarily to be construed as preferred or advantageous over other aspects.

As used herein, a phrase referring to “at least one of” a list of items refers to any combination of those items, including single members. As an example, “at least one of: a, b, or c” is intended to cover a, b, c, a-b, a-c, b-c, and a-b-c, as well as any combination with multiples of the same element (e.g., a-a, a-a-a, a-a-b, a-a-c, a-b-b, a c c, b-b, b-b-b, b-b-c, c-c, and c-c-c or any other ordering of a, b, and c).

As used herein, the term “determining” encompasses a wide variety of actions. For example, “determining” may include calculating, computing, processing, deriving, investigating, looking up (e.g., looking up in a table, a database or another data structure), ascertaining and the like. Also, “determining” may include receiving (e.g., receiving information), accessing (e.g., accessing data in a memory) and the like. Also, “determining” may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The following claims are not intended to be limited to the embodiments shown herein, but are to be accorded the full scope consistent with the language of the claims. Within a claim, reference to an element in the singular is not intended to mean “one and only one” unless specifically so stated, but rather “one or more.” Unless specifically stated otherwise, the term “some” refers to one or more. No claim element is to be construed under the provisions of 35 U.S.C. § 112(f) unless the element is expressly recited using the phrase “means for” or, in the case of a method claim, the element is recited using the phrase “step for.” All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

The following clauses describe various embodiments of the present disclosure.

Clause 1: A method, comprising: at a first time, capturing, via an Artificial Intelligence (AI) assistant device, first audio from an environment; detecting first utterances from the first audio for a patient; adding the first utterances to a language tracking model; at a second time, capturing, via the AI assistant device, second audio from the environment; detecting second utterances from the second audio for the patient; detecting via a language tracking engine provided by the AI assistant device, the language tracking model, and the second utterances, a condition change indicating a condition of the patient has changed from the first time to the second time; and generating a condition notification comprising the condition change.

Clause 2: In addition to the method of clause 1, further comprising: logging the condition notification for caretaker review; providing the condition notification to the patient for review; requesting patient permission to provide an alert to a caretaker for the patient via a call system; receiving the patient permission from the patient to provide the alert to the caretaker; and transmitting the condition notification via the call system, where the call system transmits the condition notification via a phone network to a personal device associated with the caretaker for the patient as at least one of: text message; or phone call using a synthesized voice.

Clause 3: In addition to the method of clauses 1 or 2, further comprising: at regular time intervals, transmitting, via the AI assistant device, conversation questions to the patient; capturing, via the AI assistant device, audio comprising conversation answers from the patient; adding the conversation answers to the language tracking model, and wherein detecting that the condition of the patient has changed further comprises comparing the conversation answers captured across the regular time intervals to detect changes in the conversation answers.

Clause 4: In addition to the method of clauses 1, 2, or 3, wherein detecting the condition of the patient has changed comprises: detecting, via audio associated with utterances stored in the language tracking model, a change in voice tone of the patient; associating the change in the voice tone with at least one predefined tone change indicator; and determining a change in the condition of the patient based one the at least one predefined tone change indicator.

Clause 5: In addition to the method of clauses 1, 2, 3, or 4, further comprising: detecting, via natural language processing, tracked words in the first utterances; marking the tracked words in the language tracking model with an indication for enhanced tracking; and wherein detecting the condition of the patient has changed comprises: detecting, via at least one of natural language processing or fuzzy matching processing, that a pronunciation of the tracked words has changed in the second utterances.

Clause 6: In addition to the method of clauses 1, 2, 3, 4, or 5, further comprising: determining, from the condition change, an emergency condition change indicating the patient is experiencing an emergency; providing emergency condition information to the patient via the AI assistant; generating an emergency alert via an alert system associated with the AI assistant, wherein when the alert system is a phone network, the emergency alert is sent to a personal device associated with a caretaker for the patient as at least one of: a text message; or a phone call using a synthesized voice, wherein when the alert system is part of an alert system in a group home or medical facility, the alert system transmits the emergency alert via a broadcast message to a plurality of personal devices associated with caretakers in the group home or medical facility.

Clause 7: In addition to the method of clauses 1, 2, 3, 4, 5 or 6, further comprising: detecting, using natural language processing, at least one trigger word in the first utterances; determining a baseline level for the at least one trigger word; tracking a number of uses of the at least one trigger word using the language tracking model; and wherein detecting the condition change comprises comparing the number of uses to the baseline level and predefined threshold for the at least one trigger word.

What is claimed is:

1. A method, comprising:
- at regular time intervals, transmitting, via an audio-controlled Artificial Intelligence (AI) assistant device, conversation questions to a patient, wherein the audio-controlled AI assistant device is activated by a cue phrase;
- in response to the conversation questions at a first time interval of the regular time intervals, capturing, via the audio-controlled AI assistant device, first audio from an environment;
- detecting first utterances from the first audio for the patient comprising a first set of answers to the conversation questions from the patient;
- adding the first utterances to a language tracking model;
- in response to the conversation questions at a second time interval of the regular time intervals, capturing, via the audio-controlled AI assistant device, second audio from the environment;
- detecting second utterances from the second audio for the patient comprising a second set of answers to the conversation questions from the patient;
- adding the second utterances to the language tracking model;
- detecting, via audio associated with the first utterances and the second utterances stored in the language tracking model, a change in voice tone of the patient comprising comparing changes between the first set of answers and the second set of answers;
- associating the change in the voice tone with at least one predefined tone change indicator;
- detecting via a language tracking engine provided by the audio-controlled AI assistant device, the language tracking model, and the at least one predefined tone change indicator, a condition change indicating a condition of the patient has changed from the first time interval to the second time interval;
- generating a condition notification comprising the condition change; and
- in response to the condition change:
  - activating one or more supplemental sensors to identify whether the patient is experiencing an emergency, wherein at least one of the one or more supplemental sensors is a camera; and
  - collecting sensor data from the activated one or more supplemental sensors to verify the emergency.

2. The method of claim 1, further comprising:

logging the condition notification for caretaker review;

providing the condition notification to the patient for review;

prior to transmitting the condition notification via a call system, requesting patient permission to provide an alert to a caretaker for the patient via the call system; and receiving the patient's permission from the patient to provide the alert to the caretaker, wherein the condition notification is transmitted as at least one of: a text message or a phone call using a synthesized voice.

3. The method of claim 1, further comprising:

detecting, via natural language processing, tracked words in the first utterances;

marking the tracked words in the language tracking model with an indication for enhanced tracking; and wherein detecting the condition of the patient has changed comprises:

detecting, via at least one of natural language processing or fuzzy matching processing, that a pronunciation of the tracked words has changed in the second utterances.

4. The method of claim 1, further comprising:

determining, from the condition change, an emergency condition change indicating the patient is experiencing an emergency;

providing emergency condition information to the patient via the audio-controlled AI assistant device;

generating an emergency alert via an alert system associated with the audio-controlled AI assistant device, wherein when the alert system is a phone network, the emergency alert is sent to a plurality of computing devices as at least one of:

a text message; or a phone call using a synthesized voice, wherein when the alert system is part of an alert system in a group home or medical facility, the alert system transmits the emergency alert via a broadcast message to a plurality of personal devices associated with caretakers in the group home or the medical facility.

5. The method of claim 1, further comprising:

detecting, using natural language processing, at least one trigger word in the first utterances;

determining a baseline level for the at least one trigger word;

tracking a number of uses of the at least one trigger word using the language tracking model; and wherein detecting the condition change comprises comparing the number of uses to the baseline level and predefined threshold for the at least one trigger word.

6. A non-transitory computer-readable storage medium comprising computer-readable program code that, when executed using one or more computer processors, performs an operation comprising:

at regular time intervals, transmitting, via an audio-controlled Artificial Intelligence (AI) assistant device, conversation questions to a patient, wherein the audio-controlled AI assistant device is activated by a cue phrase;

in response to the conversation questions at a first time interval of the regular time intervals, capturing, via the audio-controlled AI assistant device, first audio from an environment;

detecting first utterances from the first audio for the patient comprising a first set of answers to the conversation questions from the patient;

adding the first utterances to a language tracking model;

in response to the conversation questions at a second time interval of the regular time intervals, capturing, via the audio-controlled AI assistant device, second audio from the environment;

detecting second utterances from the second audio for the patient comprising a second set of answers to the conversation questions from the patient;

adding the second utterances to the language tracking model;

detecting, via audio associated with the first utterances and the second utterances stored in the language tracking model, a change in voice tone of the patient comprising comparing changes between the first set of answers and the second set of answers;

associating the change in the voice tone with at least one predefined tone change indicator;

detecting via a language tracking engine provided by the audio-controlled AI assistant device, the language tracking model, and the at least one predefined tone change indicator, a condition change indicating a condition of the patient has changed from the first time interval to the second time interval;

generating a condition notification comprising the condition change; and in response to the condition change:

activating one or more supplemental sensors to identify whether the patient is experiencing an emergency, wherein at least one of the one or more supplemental sensors is a camera; and collecting sensor data from the activated one or more supplemental sensors to verify the emergency.

7. The non-transitory computer-readable storage medium of claim 6, wherein the operation further comprises:

logging the condition notification for caretaker review;

providing the condition notification to the patient for review;

prior to transmitting the condition notification via a call system, requesting patient permission to provide an alert to a caretaker for the patient via the call system; and receiving the patient's permission from the patient to provide the alert to the caretaker, wherein the condition notification is transmitted as at least one of: a text message or a phone call using a synthesized voice.

8. The non-transitory computer-readable storage medium of claim 6, wherein the operation further comprises:

detecting, via natural language processing, tracked words in the first utterances;

marking the tracked words in the language tracking model with an indication for enhanced tracking; and wherein detecting the condition of the patient has changed comprises:

detecting, via at least one of natural language processing or fuzzy matching processing, that a pronunciation of the tracked words has changed in the second utterances.

9. The non-transitory computer-readable storage medium of claim 6, wherein the operation further comprises:

determining, from the condition change, an emergency condition change indicating the patient is experiencing an emergency;

providing emergency condition information to the patient via the audio-controlled AI assistant device;

generating an emergency alert via an alert system associated with the audio-controlled AI assistant device, wherein when the alert system is a phone network, the emergency alert is sent to a plurality of computing devices as at least one of:

a text message; or a phone call using a synthesized voice, wherein when the alert system is part of an alert system in a group home or medical facility, the alert system transmits the emergency alert via a broadcast message to a plurality of personal devices associated with caretakers in the group home or the medical facility.

10. The non-transitory computer-readable storage medium of claim 6, wherein the operation further comprises:

detecting, using natural language processing, at least one trigger word in the first utterances;

determining a baseline level for the at least one trigger word;

tracking a number of uses of the at least one trigger word using the language tracking model; and wherein detecting the condition change comprises comparing the number of uses to the baseline level and predefined threshold for the at least one trigger word.

11. An audio-controlled Artificial Intelligence (AI) assistant device comprising:

one or more computer processors; and a memory containing a program which when executed by the computer processors performs an operation comprising:

at regular time intervals, transmitting, via the audio-controlled AI assistant device, conversation questions to a patient, wherein the audio-controlled AI assistant device is activated by a cue phrase;

in response to the conversation questions at a first time interval of the regular time intervals, capturing, via the audio-controlled AI assistant device, first audio from an environment;

detecting first utterances from the first audio for the patient comprising a first set of answers to the conversation questions from the patient;

adding the first utterances to a language tracking model;

in response to the conversation questions at a second time interval of the regular time intervals, capturing, via the audio-controlled AI assistant device, second audio from the environment;

detecting second utterances from the second audio for the patient comprising a second set of answers to the conversation questions from the patient;

adding the second utterances to the language tracking model;

detecting, via audio associated with the first utterances and the second utterances stored in the language tracking model, a change in voice tone of the patient comprising comparing changes between the first set of answers and the second set of answers;

associating the change in the voice tone with at least one predefined tone change indicator;

detecting via a language tracking engine provided by the audio-controlled AI assistant device, the language tracking model, and the at least one predefined tone change indicator, a condition change indicating a condition of the patient has changed from the first time interval to the second time interval;

generating a condition notification comprising the condition change; and in response to the condition change:

activating one or more supplemental sensors to identify whether the patient is experiencing an emergency, wherein at least one of the one or more supplemental sensors is a camera; and collecting sensor data from the activated one or more supplemental sensors to verify the emergency.

12. The audio-controlled AI assistant device of claim 11, wherein the operation further comprises:

logging the condition notification for caretaker review;

providing the condition notification to the patient for review;

prior to transmitting the condition notification via a call system, requesting patient permission to provide an alert to a caretaker for the patient via the call system; and receiving the patient's permission from the patient to provide the alert to the caretaker, wherein the condition notification is transmitted as at least one of: a text message or a phone call using a synthesized voice.

13. The audio-controlled AI assistant device of claim 11, wherein the operation further comprises:

detecting, via natural language processing, tracked words in the first utterances;

marking the tracked words in the language tracking model with an indication for enhanced tracking; and wherein detecting the condition of the patient has changed comprises:

detecting, via at least one of natural language processing or fuzzy matching processing, that a pronunciation of the tracked words has changed in the second utterances.

14. The audio-controlled AI assistant device of claim 11, wherein the operation further comprises:

determining, from the condition change, an emergency condition change indicating the patient is experiencing an emergency;

providing emergency condition information to the patient via the audio-controlled AI assistant device;

generating an emergency alert via an alert system associated with the audio-controlled AI assistant device, wherein when the alert system is a phone network, the emergency alert is sent to a plurality of computing devices as at least one of:

a text message; or a phone call using a synthesized voice, wherein when the alert system is part of an alert system in a group home or medical facility, the alert system transmits the emergency alert via a broadcast message to a plurality of personal devices associated with caretakers in the group home or the medical facility.

* * * * *